(12) United States Patent
Flohr et al.

(10) Patent No.: US 7,425,551 B2
(45) Date of Patent: Sep. 16, 2008

(54) MALONAMIDE DERIVATIVES

(75) Inventors: Alexander Flohr, Reinach BL (CH);
Roland Jakob-Roetne, Inzlingen (DE);
Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/726,639

(22) Filed: Mar. 22, 2007

(65) Prior Publication Data

US 2007/0225273 A1 Sep. 27, 2007

(30) Foreign Application Priority Data

Mar. 27, 2006 (EP) .................................. 06111771

(51) Int. Cl.
*C07D 223/18* (2006.01)
*A61K 31/55* (2006.01)
(52) U.S. Cl. .................... 514/212.04; 540/522
(58) Field of Classification Search ................ 540/522; 514/212.04
See application file for complete search history.

(56) References Cited

FOREIGN PATENT DOCUMENTS

| WO | WO 01/77086 A1 | 10/2001 |
|---|---|---|
| WO | WO 01/92235 A1 | 12/2001 |
| WO | WO 2004/069826 | 8/2004 |
| WO | WO 2005/023772 | 3/2005 |
| WO | WO 2005/040126 | 5/2005 |

OTHER PUBLICATIONS

Sisodia et al., Nature Reviews/Neuroscience vol. 3, Apr. 2002, pp. 281-290.
Beher et al., Biochemical Society Transactions (2002), vol. 30, Part 4, pp. 534-537.
Wolfe M., Current Topics in Medicinal Chemistry, 2002, 2, pp. 371-383.
Tsai et al., Current Medicinal Chemistry, 2002, col. 9, No. 11, pp. 1087-1106.
Sambamurti et al., Drug Development Research, vol. 56, 2002, pp. 211-227.
May, P.C., Drug Discovery Today, vol. 6, No. 9, May 2001, pp. 459-462.
Nunan et al., FEBS Letters, 483 (2000) pp. 6-10.
Hardy et al., Science vol. 297, 2002, pp. 353-356.
Wolfe M., Journal of Medicinal Chemistry, vol. 44, No. 13 (2001) pp. 2039-2060.
Brockhaus, et al., Neuroreport 9(7) pp. 1481-1486 (1998).

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to malonamide derivatives of formula

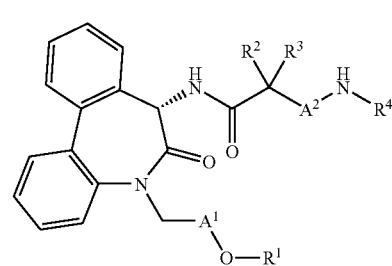

I wherein
$A^1$, $A^2$, $R^1$, $R^2$, $R^3$, and $R^4$ are as defined herein and to pharmaceutically acceptable acid addition salts, optically pure enantiomers, racemates or diastereomeric mixtures thereof for the treatment of Alzheimer's disease.

10 Claims, No Drawings

MALONAMIDE DERIVATIVES

PRIORITY TO RELATED APPLICATIONS

This application claims the benefit of European Application No. 06111771.9, filed Mar. 27, 2006 which is hereby incorporated by reference in its entirety.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length. Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and can represent a new group of atypical aspartyl proteases which cleave within the TM of their substrates and which are themselves polytopic membrane proteins. Other essential components of γ-secretase can be nicastrin and the products of the aph1 and pen-2 genes. Proven substrates for γ-secretase are the APP and the proteins of the Notch receptor family, however, γ-secretase has a loose substrate specificity and can cleave further membrane proteins unrelated to APP and Notch.

The γ-secretase activity is absolutely required for the production of Abeta peptides. This has been shown both by genetic means, i.e., ablation of the presenilin genes and by low-molecular-weight inhibitory compounds. Since according to the amyloid hypothesis or AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:
Nature Reviews/Neuroscience, Vol. 3, April 2002/281,
Biochemical Society Transactions (2002), Vol. 30. part 4,
Current Topics in Medicinal Chemistry, 2002, 2, 371-383,
Current Medicinal Chemistry, 2002, Vol. 9, No. 11, 1087-1106,
Drug Development Research, 56, 211-227, 2002,
Drug Discovery Today, Vol. 6, No. 9, May 2001, 459-462,
FEBS Letters, 483, (2000), 6-10,
Science, Vol. 297, 353-356, July 2002 and
Journ. of Medicinal Chemistry, Vol. 44, No. 13, 2001, 2039-2060.

SUMMARY OF THE INVENTION

The invention provides malonamide derivatives of formula I

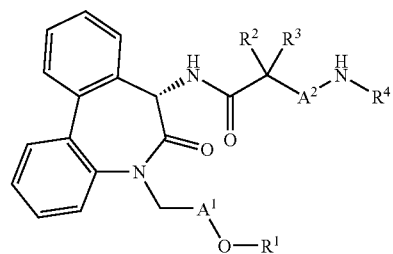

wherein
$A^1$ is —CHR— or —C(O)—;
$A^2$ is —C(O)— and
$R^2$ and $R^3$ are each independently hydrogen, lower alkyl, halogen, hydroxy or lower alkoxy;
or
$A^2$ is —O—C(O)— and
$R^2$ and $R^3$ are each independently hydrogen or lower alkyl;
R is hydrogen or lower alkyl substituted by halogen;
$R^1$ is hydrogen, or is lower alkyl or —(CH$_2$)$_n$-aryl, each of which is optionally substituted by halogen;
$R^4$ is lower alkyl substituted by halogen; and
n is 0, 1 or 2;

and pharmaceutically suitable acid addition salts, optically pure enantiomers, racemates or diastereomeric mixtures thereof.

The invention also provides all forms of optically pure enantiomers, racemates or diastereomeric mixtures for compounds of formula I.

The invention further provides pharmaceutical compositions containing one ore more compound of formula I or their pharmaceutically acceptable salts thereof and a pharmaceutically acceptable carrier. The present invention also provides methods for the manufacture of compounds of the invention and the compositions containing them.

Compounds of formula I are γ-secretase inhibitors and can be useful in the treatment of Alzheimer's disease, for example, by blocking the activity of γ-secretase and reducing or preventing the formation of the various amyloidogenic Abeta peptides. The advantage of compounds of formula I for use in a drug is their good solubility in comparison with compounds, disclosed in WO2004/069826, WO 2005/023772 and WO2005/040126. Furthermore, the present compounds may be used for the treatment of all forms of cancer.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "lower alkoxy" denotes an alkyl group as defined above, which is attached via an oxygen atom.

The term "halogen" denotes fluorine, chlorine, bromine, and iodine.

The term "lower alkyl substituted by halogen" denotes an alkyl group as defined above, wherein at least one hydrogen atom is replaced by a halogen atom, for example $CF_3$, $CHF_2$, $CH_2F$, $CH_2CF_3$, $CH_2CH_2F$, $CH_2CF_2CF_3$, $CH_2CH_2CF_2CF_3$ $CH_2CH_2CF_3$ and the like.

The term "aryl" denotes a monovalent cyclic aromatic hydrocarbon radical having from 6 to 10 ring atoms, for example phenyl, naphthyl, biphenyl or indanyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The invention provides malonamide derivatives of formula I

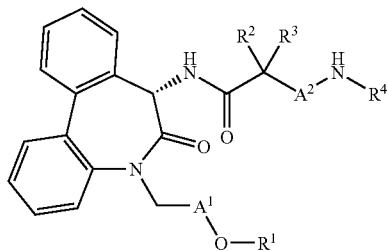

I wherein
$A^1$ is —CHR— or —C(O)—;
$A^2$ is —C(O)— and
$R^2$ and $R^3$ are each independently hydrogen, lower alkyl, halogen, hydroxy or lower alkoxy; or
$A^2$ is —O—C(O)— and
$R^2$ and $R^3$ are each independently hydrogen or Lower alkyl;
R is hydrogen or lower alkyl substituted by halogen;
$R^1$ is hydrogen, or is lower alkyl or —$(CH_2)_n$-aryl, each of which is optionally substituted by halogen;
$R^4$ is lower alkyl substituted by halogen; and
n is 0, 1 or 2;

and pharmaceutically suitable acid addition salts, optically pure enantiomers, racemates or diastereomeric mixtures thereof.

The invention also provides all forms of optically pure enantiomers, racemates or diastereomeric mixtures for compounds of formula I.

The most preferred compounds of formula I are those, wherein $A^1$ is $CH_2$, $A^2$ is CO, $R^1$ is hydrogen or lower alkyl, for example the following compounds:

N—[(S)-5-(2-hydroxy-ethyl)-6-oxo-6,7-dihydro-5H-dibenzo[b,d]azepin-7-yl]-2-methyl -N'-(2,2,3,3,3-pentafluoro-propyl)-malonamide, N—[(S)-5-(2-hydroxy-ethyl)-6-oxo-6,7-dihydro-5H-dibenzo[b,d]azepin-7-yl]-2,2-dimethyl -N'-(2,2,3,3,3-pentafluoro-propyl)-malonamide, N—[(S)-5-(2-hydroxy-ethyl)-6-oxo-6,7-dihydro-5H-dibenzo[b,d]azepin-7-yl]-N-(2,2,3,3,3-pentafluoro-propyl)-malonamide, N—[(S)-5-(2-hydroxy-ethyl)-6-oxo-6,7-dihydro-5H-dibenzo[b,d]azepin-7-yl]-2-methoxy -N'-(2,2,3,3,3-pentafluoro-propyl)-malonamide, 2-hydroxy-N—[(S)-5-(2-hydroxy-ethyl)-6-oxo-6,7-dihydro-5H-dibenzo[b,d]azepin-7-yl]-2 -methyl-N'-(2,2,3,3,3-pentafluoro-propyl)-malonamide, 2-fluoro-N—[(S)-5-(2-hydroxy-ethyl)-6-oxo-6,7-dihydro-5H-dibenzo[b,d]azepin-7-yl]-2-methyl -N'-(2,2,3,3,3-pentafluoro-propyl)-malonamide, 2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, (S or R)-2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, epimer A,

[R or S]2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, epimer B, 2-hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide, epimer A, 2-hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide epimer B, N—[(S)-5-(2-methoxy-ethyl)-6-oxo-6,7-dihydro-5H-dibenzo[b,d]azepin-7-yl]-N'-(2,2,3,3,3-pentafluoro-propyl)-malonamide, (R)-2-fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide, (S)-2-fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide, N—[(S)-5-(2-hydroxy-ethyl)-6-oxo-6,7-dihydro-5H-dibenzo[b,d]azepin-7-yl]-N'-(3,3,3-trifluoro-propyl)-malonamide, N—[(S)-5-(2-hydroxy-ethyl)-6-oxo-6,7-dihydro-5H-dibenzo[b,d]azepin-7-yl]-N'-(3,3,4,4,4-pentafluoro-butyl)-malonamide, (R)-2-fluoro-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, (R)-2-fluoro-N—[(S)-5-(2-hydroxy-ethyl)-6-oxo-6,7-dihydro-5H-dibenzo[b,d]azepin-7-yl]-2-methyl-N-(2,2,2-trifluoro-ethyl)-malonamide, (R)-2-fluoro-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, 2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, (R)-2-hydroxy-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide, (S)-2-hydroxy-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide, (R or S)-2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, epimer A, (S or R)-2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, epimer B, 2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, (R or S)-2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, epimer A and (S or R)-2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, epimer B.

Preferred compounds are further those, wherein $A^1$ is $CH_2$, $A^2$ is O—CO and $R^1$ is hydrogen or lower alkyl, for example the following compounds:

(2,2,3,3,3-pentafluoro-propyl)-carbamic acid (S)-1-[(S)-5-(2-hydroxy-ethyl)-6-oxo-6,7-dihydro-5H-dibenzo[b,d]azepin-7-ylcarbamoyl]-ethyl ester, (2,2,3,3,3-pentafluoro-propyl)-carbamic acid (S)-1-[(S)-5-(2-methoxy-ethyl)-6-oxo-6,7-dihydro-5H-dibenzo[b,d]azepin-7-ylcarbamoyl]-ethyl ester, (3,3,4,4,4-pentafluoro-butyl)-carbamic acid (S)-1-[(S)-5-(2-hydroxy-ethyl)-6-oxo-6,7-dihydro-5H-dibenzo[b,d]azepin-7-ylcarbamoyl]-ethyl ester, (3,3,3-trifluoro-propyl)-carbamic acid (S)-1-[(S)-5-(2-hydroxy-ethyl)-6-oxo-6,7-dihydro-5H-dibenzo[b,d]azepin-7-ylcarbamoyl]-ethyl ester, (2-fluoro-ethyl)-carbamic acid (S)-1-[(S)-5-(2-hydroxy-ethyl)-6-oxo-6,7-dihydro-5H-dibenzo[b,d]azepin-7-ylcarbamoyl]-ethyl ester, and (2,2,2-trifluoro-ethyl)-carbamic acid (S)-1-[(S)-5-(2-hydroxy-ethyl)-6-oxo-6,7-dihydro-5H-dibenzo[b,d]azepin-7-ylcarbamoyl]-ethyl ester.

Preferred compounds are further those, wherein $A^1$ is $CHCF_3$, $A^2$ is CO and $R^1$ is hydrogen or lower alkyl, for example the following compound:

2,2-dimethyl-N—[(S)-6-oxo-5-(3,3,3-trifluoro-2-hydroxy-propyl)-6,7-dihydro-5H-dibenzo[b,d]azepin-7-yl]-N'-(2,2,3,3,3-pentafluoro-propyl)-malonamide.

The present compounds of formula I and their pharmaceutically acceptable salts can be prepared by methods known in the art, for example, by processes described below, which processes comprise a) reacting a compound of formula

II with a compound of formula $NH_2R^4$

III to obtain a compound of formula

I wherein $A^1$ and $R^1$-$R^4$ have the meaning as described above and $A^2$ depicts CO, and if desired, converting the compounds obtained into pharmaceutically acceptable acid addition salts.

or b) reacting a compound of formula

IV with a compound of formula

V to obtain a compound of formula

I wherein $A^1$ and $R^1$-$R^4$ have the meaning as described above and $A^2$ depicts CO, and if desired, converting the compounds obtained into pharmaceutically acceptable acid addition salts.

or c) reacting a compound of formula

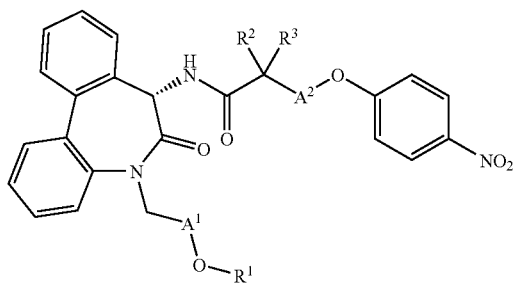

with a compound of formula

NH$_2$R$^4$   III to obtain a compound of formula

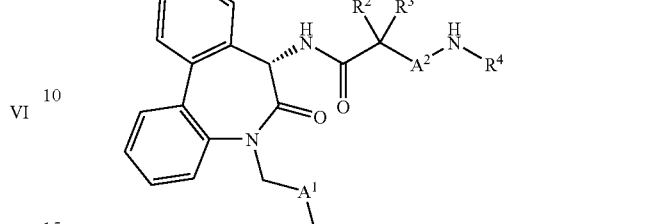

wherein A$^1$ and R$^1$-R$^4$ have the meaning as described above and A$^2$ depicts O—CO, and if desired, converting the compounds obtained into pharmaceutically acceptable acid addition salts.

The detailed description can be found below and in Examples 1-73. The starting materials of formulas III, V, VIII, X, XI, XIII and XIV are known compounds or can be prepared by methods well-known in the art. The amines of formula III are commercial available products.

Scheme I

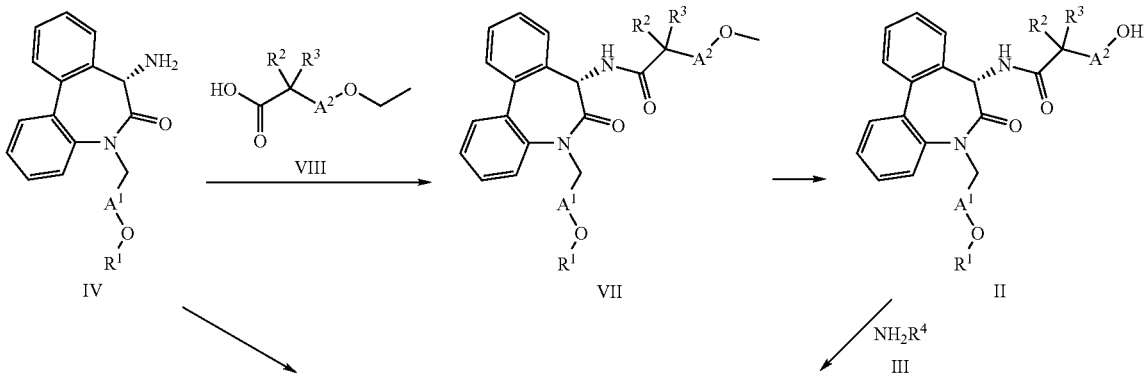

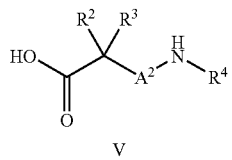

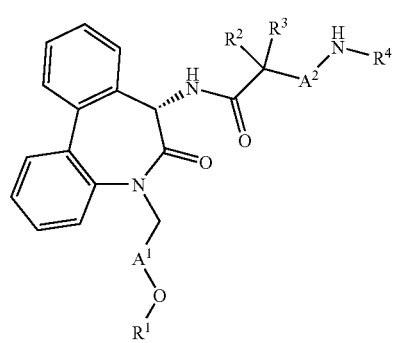

In this scheme $A^1$ and $R^1$-$R^3$ are as described above and $A^2$ depicts CO;

Scheme 2

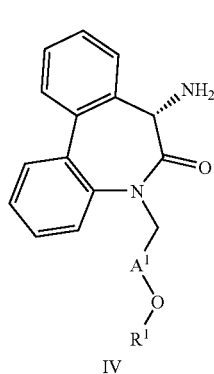

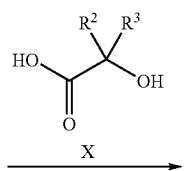

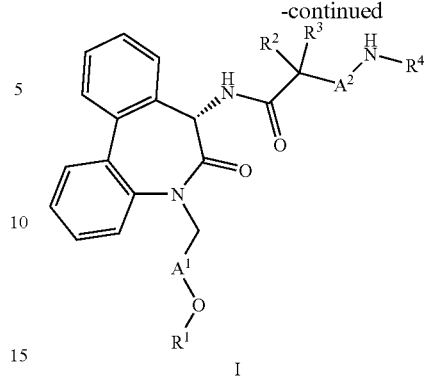

I

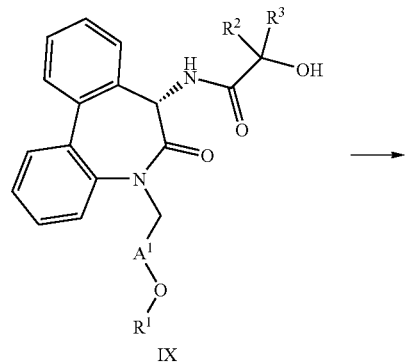

IX

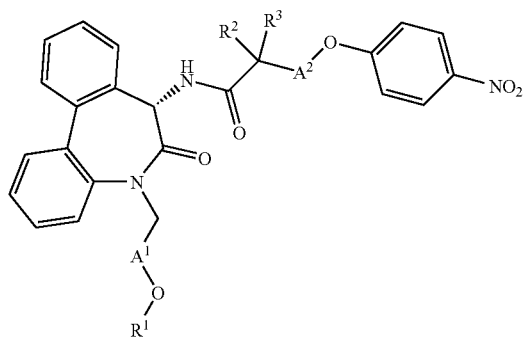

VI

III

In this scheme $A^1$ and $R^1$-$R^3$ are as described above and $A^2$ depicts O—CO;

In accordance with scheme 1 a compound of formula II can be prepared as follows:

To a solution of a compound of formula IV, for example (S)-7-amino-5-(2-benzyloxy-ethyl)-5H,7H-dibenzo[b,d]azepin-6-one and an acid of formula VIII, for example (S)-2-fluoro-2-methyl-malonic acid monoethyl ester in THF is added 1-hydroxybenzotriazole, N-ethyldiisopropylamine and N-(3-dimethylaminopropyl)-N'-ethylcarbodiimide hydrochloride (EDC), and the mixture is stirred for 2.5 hours at r.t. The reaction mixture is quenched with water and ethyl acetate, the two phases are separated and the organic layer is washed, dried and purified in the usual manner.

Then compound of formula VII, for example (S)-7-amino-5-(2-benzyloxy-ethyl)-5H,7H-dibenzo[b,d]azepin-6-one and 2,2-dimethyl-malonic acid monoethyl ester is then dissolved in THF and treated with LiOH and water for 18 hours at r.t. Workup and purification in the usual manner afford the compound of formula II. This obtained compound and a compound of formula III, for example 2,2,3,3,3-pentafluoropropylamine are dissolved in THF, treated with 1-hydroxybenzotriazole, N-ethyldiisopropylamine and EDC and the mixture is stirred for 2.5 hours at r.t. The obtained compound of formula I is isolated and purified in conventional manner.

In accordance with scheme 2 a compound of formula I can be prepared as follows:

To a cooled solution of a compound of formula IV, for example (S)-7-amino-5-(2-benzyloxy-ethyl)-5H,7H-dibenzo[b,d]azepin-6-one and an acid, for example L-(+)-lactic acid, in THF is added 1-hydroxybenzotriazole, N-(3-dimethylaminopropyl)-N'-ethylcarbodiimide hydrochloride (EDC) and N-ethyldiisopropylamine, and the mixture is stirred for 0.5 hours at 0° C. and 3 hours at r.t. The reaction mixture is quenched with water/ethyl acetate. Washing, drying and purification in the usual manner affords a compound of formula IX.

Then compound of formula IX, for example (S)—N—[(S)-5-(2-benzyloxy-ethyl)-6-oxo-6,7-dihydro-5H-dibenzo[b,d]azepin-7-yl]-2-hydroxy-propionamide, is dissolved in dichloromethane and reacted with 4-nitrophenyl-chloroformate and pyridine for 7 hours. Workup and purification in the usual manner afford the compound of formula VI. This obtained compound and a compound of formula III, for example 2,2,3,3,3-pentafluoropropylamine are reacted for 24 hours at r.t. After evaporation of all volatile components, purification in the usual manner affords a compound of formula I.

Scheme 3

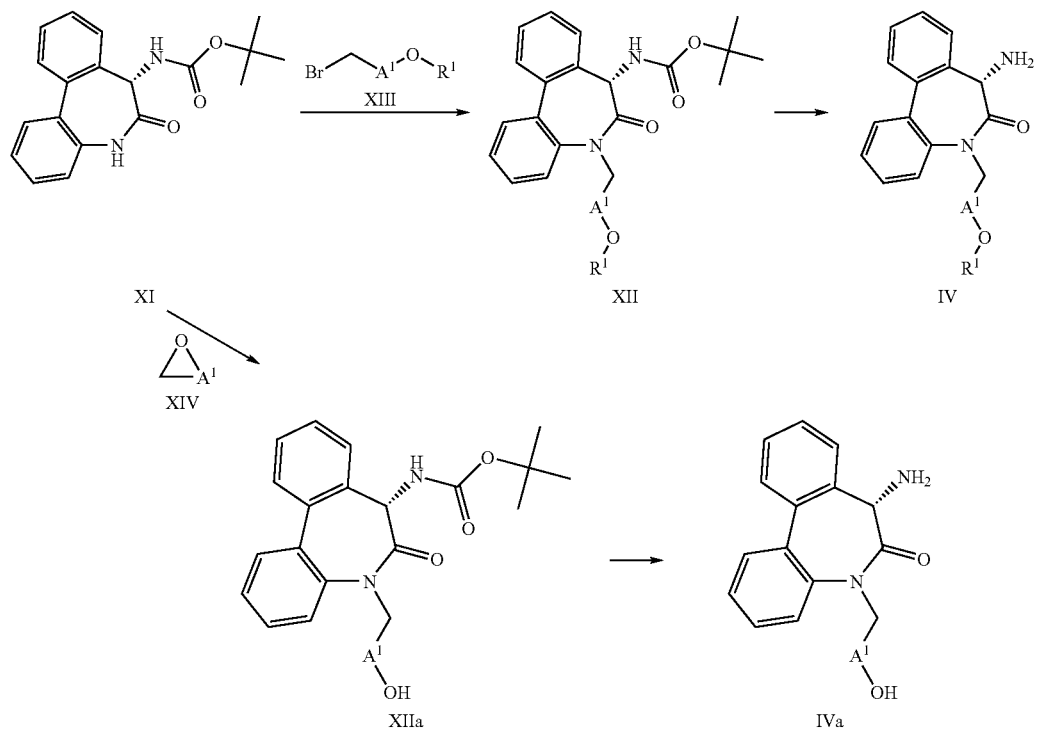

In this scheme $A^1$ and $R^1$ are as described above;

In accordance with scheme 3 a compound of formula IV can be prepared as follows:

A compound of formula XI, for example ((S)-6-oxo-6,7-dihydro-5H-dibenzo[b,d]azepin-7-yl)-carbamic acid tert-butyl ester is dissolved in DMF and treated with sodium hydride. After stirring for 0.5 hours, a compound of formula XII, for example benzyl 2-bromoethyl ether is added and the reaction mixture stirred for 6 hours. Alternatively, a compound of formula XI, for example ((S)-6-oxo-6,7-dihydro-5H-dibenzo[b,d]azepin-7-yl)-carbamic acid tert-butyl ester is dissolved with a compound of formula XIV, for example 1,1,1-trifluoro-2,3-epoxypropane in DMF and stirred for 22 hours at 90° C. Washing, drying and purification in the usual manner afford a compound of formula XIIa.

Then compound of formula XIIa and trifluoroacetic acid are dissolved in dichloromethane and stirred for 3 hours at r.t. Workup and purification in the usual manner affords the compound of formula IVa.

Compounds of formula I can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, compounds of the present invention can inhibit γ-secretase.

The compounds were investigated in accordance with the test given hereinafter.

Description of 1γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6× Histidin tail for purification which is expressed in *E. coli* in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138-6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998).

The preferred compounds show a $IC_{50}$<0.1 (μM). The list below provides data of γ-secretase inhibition for representative compounds:

| Example No. | $IC_{50}$ in vitro |
|---|---|
| 1 | 0.010 |
| 2 | 0.006 |
| 3 | 0.001 |
| 4 | 0.009 |
| 5 | 0.011 |
| 6 | 0.002 |
| 7 | 0.022 |
| 8 | 0.006 |
| 9 | 0.019 |
| 10 | 0.049 |
| 11 | 0.007 |
| 12 | 0.010 |
| 13 | 0.010 |
| 14 | 0.008 |
| 15 | 0.001 |
| 16 | 0.003 |
| 17 | 0.004 |
| 18 | 0.007 |
| 19 | 0.004 |
| 20 | 0.003 |
| 21 | 0.001 |
| 22 | 0.002 |
| 23 | 0.016 |
| 24 | 0.034 |
| 25 | 0.006 |
| 26 | 0.001 |
| 27 | 0.004 |
| 28 | 0.068 |
| 29 | 0.018 |
| 30 | 0.075 |
| 31 | 0.200 |
| 32 | 0.018 |
| 33 | 0.004 |
| 34 | 0.004 |
| 35 | 0.022 |
| 36 | 0.013 |
| 37 | 0.018 |
| 38 | 0.012 |
| 39 | 0.016 |
| 40 | 0.005 |
| 41 | 0.480 |
| 42 | 0.001 |
| 43 | 0.013 |
| 44 | 0.009 |
| 45 | 0.009 |
| 46 | 0.002 |
| 47 | 0.755 |
| 48 | 0.014 |
| 49 | 0.157 |
| 50 | 0.016 |
| 51 | 0.007 |
| 52 | 0.010 |
| 53 | 0.009 |
| 54 | 0.008 |
| 55 | 0.012 |
| 56 | 0.002 |
| 57 | 0.090 |
| 58 | 0.008 |
| 59 | 0.190 |
| 60 | 0.004 |
| 61 | |
| 62 | 0.001 |
| 63 | 0.002 |
| 64 | 0.010 |
| 65 | 0.039 |
| 66 | 0.001 |
| 67 | 0.005 |
| 68 | 0.009 |
| 69 | 0.006 |
| 70 | 0.007 |
| 71 | 0.006 |
| 72 | 0.001 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

In accordance with the invention compounds of formula I as well as their pharmaceutically acceptable salts are useful in the treatment or prevention of illnesses based on the inhibition of the γ-secretase, such as of Alzheimer's disease. The invention, therefore, provides a method for treating Alzheimer's disease which comprises administering a therapeutically effective amount of a compound of formula I or a pharmaceutically acceptable salt thereof and a pharmaceutically acceptable carrier.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injection solutions.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| | Tablet Formulation (Wet Granulation) mg/tablet | | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation mg/capsule | | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |

-continued

| | Capsule Formulation mg/capsule | | | | |
|---|---|---|---|---|---|
| Item | Ingredients | 5 mg | 25 mg | 100 mg | 500 mg |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples are provided for illustration of the invention. They should not be considered as limiting the scope of the invention, but merely as being representative thereof. Unless otherwise indicated, the following examples have been performed, regardless of the tense in which they are written.

EXAMPLE 1

{(S)-6-Oxo-7-[2-(2,2,3,3,3-pentafluoro-propylcarbamoyl)-propionylamino]-6,7-dihydro-dibenzo[b,d]azepin-5-yl}-acetic acid methyl ester a) ((S)-7-tert.-Butoxycarbonylamino-6-oxo-6,7-dihydro-dibenzo[b,d]azepin-5-yl)-acetic acid methyl ester

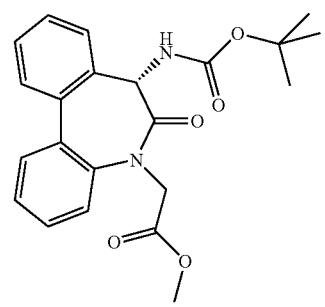

Chiral ((S)-6-Oxo-6,7-dihydro-5H-dibenzo[b,d]azepin-7-yl)-carbamic acid tert-butyl ester (284 mg, 0.88 mmol) were diluted in DMF (5 ml) and treated with sodium hydride (60 mg of 60% suspension in mineral oil, 1.5 mmol). After stirring for 30 minutes, methyl bromoacetate (0.14 ml, 1.5 mmol) were added and the solution stirred for another 6 h. The pH is adjusted to 1.5 with 2N hydrogen chloride and extracted with ethyl acetate (10 ml). After back-extraction of the aqueous phases with ethyl acetate, the combined organic phases were washed with water and saturated aqueous sodium chloride, dried over magnesium sulfate and evaporated to dryness. After chromatography (silica, eluent cyclohexane/ethyl acetate 88/12), the product was obtained as off-white viscous oil (63%); MS: m/e=397(M+H$^+$).

b) ((S)-7-Amino-6-oxo-6,7-dihydro-dibenzo[b,d]azepin-5-yl)-acetic acid methyl ester

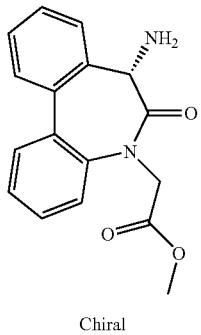

Chiral ((S)-7-tert-Butoxycarbonylamino-6-oxo-6,7-dihydro-dibenzo[b,d]azepin-5-yl)-acetic acid methyl ester (60 mg, 0.15 mmol) were dissolved in dichloromethane (3 ml), treated with 0.15 ml (2.3 mmol) orthophosphoric acid and stirred for 18 .h The reaction mixture is adjusted to pH 7.5 with 2N aqueous sodium hydroxide, diluted with dichloromethane (5 ml) and the phases separated. After extraction of the organic phases with water (5 ml) and saturated aqueous sodium chloride (5 ml), the solution is dried with magnesium sulfate and evaporated to dryness. White solid (60%); MS: m/e=297(M+H+), which was used without further purification.

c) {(S)-6-Oxo-7-[2-(2,2,3,3,3-pentafluoro-propylcarbamoyl)-propionylamino]-6,7-dihydro-dibenzo[b,d]azepin-5-yl}-acetic acid methyl ester

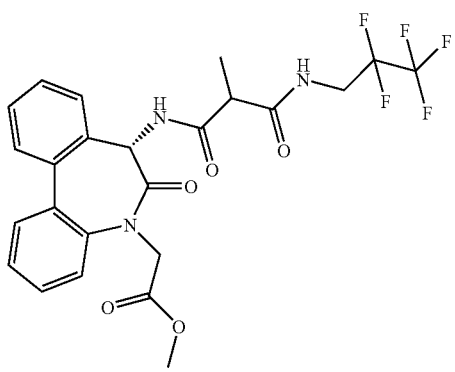

((S)-7-Amino-6-oxo-6,7-dihydro-dibenzo[b,d]azepin-5-yl)-acetic acid methyl ester (25 mg, 0.85 mmol) were dissolved in THF and subsequently treated with 2-methyl-N-(2,2,3,3,3-pentafluoro-propyl)-malonamic acid (25 mg, 0.1 mmol), 1-hydroxybenzotriazole (11.6 mg, 0.85 mmol), N-ethyldiisopropylamine (0.03 ml, 0.17 mmol) and EDC (16.5 mg, 0.85 mmol). After stirring for 2.5 h at ambient temperature, the reaction mixture is quenched with water and extracted with ethyl acetate. The aqueous phase is extracted twice with ethyl acetate and the combined organic layers are extracted with water (2×5 ml) and saturated aqueous sodium chloride (5 ml), combined, dried over anhydrous sodium sulfate and evaporated to dryness. Chromatography (silica, eluent cyclohexane/ethyl acetate 65/35) afforded the product as colorless solid (70%). MS: m/e=528 (M+H+).

EXAMPLE 2

N—[(S)-5-(2-Benzyloxy-ethyl)-6-oxo-6,7-dihydro-5H-dibenzo[b,d]azepin-7-yl]-2-methyl-N'-(2,2,3,3,3-pentafluoro-propyl)-malonamide a) [(S)-5-(2-Benzyloxy-ethyl)-6-oxo-6,7-dihydro-5H-dibenzo[b,d]azepin-7-yl]-carbamic acid tert-butyl ester

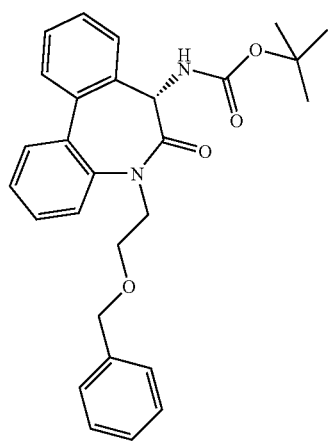

Chiral

Using ((S)-6-oxo-6,7-dihydro-5H-dibenzo[b,d]azepin-7-yl)-carbamic acid tert-butyl ester and benzyl 2-bromoethyl ether, the title compound was prepared in the same manner as described for example 1a. White crystals, mp. 132-134° C. (84%). MS: m/e=459(M+H+), mp 133° C.

b) (S)-7-Amino-5-(2-benzyloxy-ethyl)-5H,7H-dibenzo[b,d]azepin-6-one

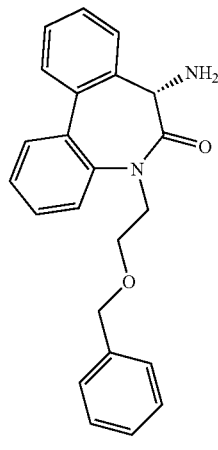

Chiral

Using [(S)-5-(2-benzyloxy-ethyl)-6-oxo-6,7-dihydro-5H-dibenzo[b,d]azepin-7-yl]-carbamic acid tert-butyl ester, the title compound was prepared in the same manner as described for example 1b). Light yellow, viscous oil (>98%). MS: m/e=359(M+H⁺).

c) N—[(S)-5-(2-Benzyloxy-ethyl)-6-oxo-6,7-dihydro-5H-dibenzo[b,d]azepin-7-yl]-2-methyl-N'-(2,2,3,3,3-pentafluoro-propyl)-malonamide

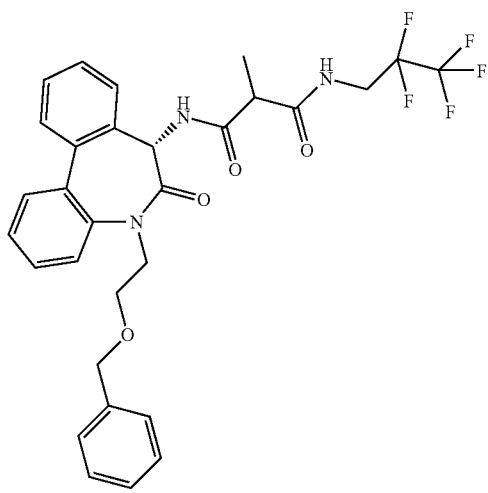

Using (S)-7-amino-5-(2-benzyloxy-ethyl)-5H,7H-dibenzo[b,d]azepin-6-one and 2-methyl-N-(2,2,3,3,3-pentafluoro-propyl)-malonamic acid, the title compound was prepared in the same manner as described for example 1c). White solid (89% yield). MS: m/e=490(M+H⁺).

EXAMPLE 3

N—[(S)-5-(2-Hydroxy-ethyl)-6-oxo-6,7-dihydro-5H-dibenzo[b,d]azepin-7-yl]-2-methyl-N'-(2,2,3,3,3-pentafluoro-propyl)-malonamide

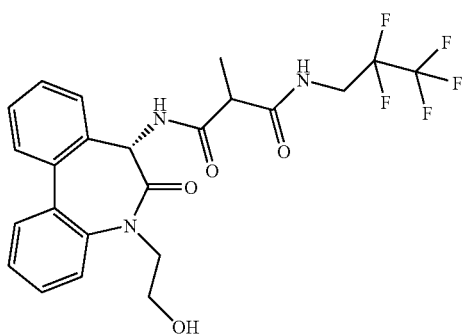

N—[(S)-5-(2-Benzyloxy-ethyl)-6-oxo-6,7-dihydro-5H-dibenzo[b,d]azepin-7-yl]-2-methyl-N'-(2,2,3,3,3-pentafluoro-propyl)-malonamide (113 mg, 0.19 mmol) were dissolved in methanol (20 ml) and treated with 37% aqueous HCl (0.1 ml) and palladium on carbon (10%, 6 mg) and stirred for 2 days under an atmosphere of hydrogen. After filtration and evaporation of the solvent, the title compound was obtained as white solid (94%). MS: m/e=450(M+H⁺).

EXAMPLE 4

N—[(S)-5-(2-Benzyloxy-ethyl)-6-oxo-6,7-dihydro-5H-dibenzo[b,d]azepin-7-yl]-2,2-dimethyl-N'-(2,2,3,3,3-pentafluoro-propyl)-malonamide a) N—[(S)-5-(2-Benzyloxy-ethyl)-6-oxo-6,7-dihydro-5H-dibenzo[b,d]azepin-7-yl]-2,2-dimethyl-malonamic acid ethyl ester

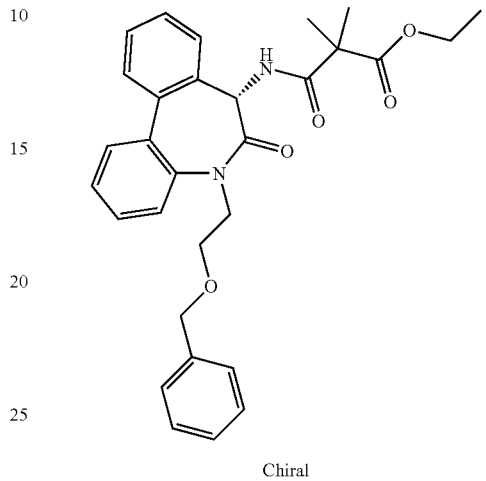

Chiral

Using (S)-7-amino-5-(2-benzyloxy-ethyl)-5H,7H-dibenzo[b,d]azepin-6-one and 2,2-dimethyl-malonic acid monoethyl ester, the title compound was prepared in the same manner as described for example 1c. Colorless oil (>98%). MS: m/e=501(M+H⁺).

b) N—[(S)-5-(2-Benzyloxy-ethyl)-6-oxo-6,7-dihydro-5H-dibenzo[b,d]azepin-7-yl]-2,2-dimethyl-malonamic acid

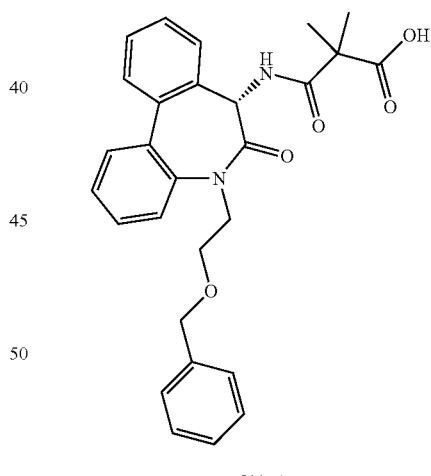

Chiral

N—[(S)-5-(2-Benzyloxy-ethyl)-6-oxo-6,7-dihydro-5H-dibenzo[b,d]azepin-7-yl]-2,2-dimethyl-malonamic acid ethyl ester (127 mg, 0.25 mmol) were dissolved in THF (4.5 ml) and water (1.1 ml), treated with lithium hydroxide (25 mg, 1 mmol) and stirred for 18 h at ambient temperature. The mixture is diluted with aqueous saturated sodium carbonate and extracted twice with ethyl acetate. The aqueous phase is acidified with concentrated aqueous hydrogen chloride to pH 0 and extracted twice with ethyl acetate. The acidic organic layers were combined, dried over magnesium sulfate and evaporated to afford 112 mg (93%) of white foam. MS: m/e=472(M−H⁺).

c) N—[(S)-5-(2-Benzyloxy-ethyl)-6-oxo-6,7-dihydro-5H-dibenzo[b,d]azepin-7-yl]-2,2-dimethyl-N'-(2,2,3,3,3-pentafluoro-propyl)-malonamide

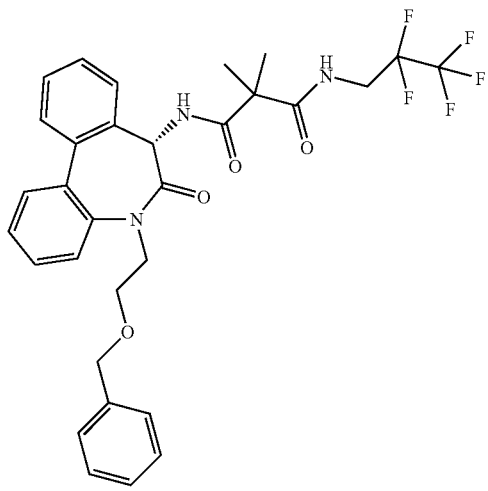

Chiral

Using N—[(S)-5-(2-benzyloxy-ethyl)-6-oxo-6,7-dihydro-5H-dibenzo[b,d]azepin-7-yl]-2,2-dimethyl-malonamic acid and 2,2,3,3,3-pentafluoropropylamine, the title compound was prepared in the same manner as described for example 1c. White solid (76%). MS: m/e=604(M+H$^+$).

EXAMPLE 5

(2,2,3,3,3-Pentafluoro-propyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester a) (S)—N—[(S)-5-(2-Benzyloxy-ethyl)-6-oxo-6,7-dihydro-5H-dibenzo[b,d]azepin-7-yl]-2-hydroxy-propionamide

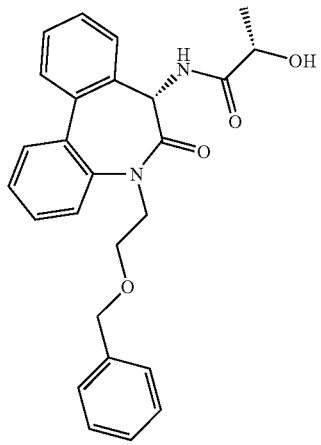

Chiral (S)-7-Amino-5-(2-benzyloxy-ethyl)-5H,7H-dibenzo[b,d]azepin-6-one (50 mg, 0.14 mmol) and L-(+)-lactic acid (14 mg, 0.15 mmol) were dissolved in THF (2 ml), cooled to 0° C. and under exclusion of moisture subsequently treated with 1-hydroxybenzotriazole (21 mg, 0.15 mmol), EDC (33 mg, 0.17 mmol) and N-diisopropyl-ethylamine (0.05 ml, 0.28 mmol). After stirring for 30 min. at 0° C. and 3 h at ambient temperature, the mixture was diluted with water and ethyl acetate (10 ml each), the phases separated and the organic layer extracted with water, 1N aqueous HCl and saturated aqueous NaCl. After drying over magnesium sulphate and evaporation of the solvent, the title compound was afforded as colourless oil (98%). MS: m/e=431(M−H$^+$).

b) Carbonic acid (S)-1-[(S)-5-(2-benzyloxy-ethyl)-6-oxo-6,7-dihydro-5H-dibenzo[b,d]azepin-7-ylcarbamoyl]-ethyl ester 4-nitro-phenyl ester

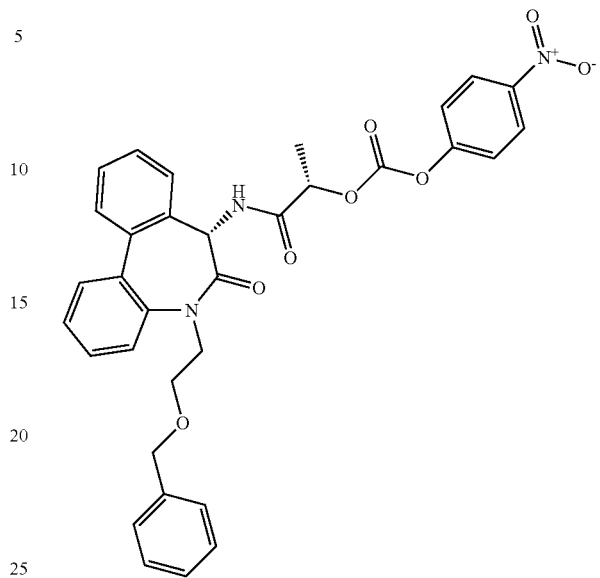

Chiral (S)—N—[(S)-5-(2-Benzyloxy-ethyl)-6-oxo-6,7-dihydro-5H-dibenzo[b,d]azepin-7-yl]-2-hydroxy-propionamide (113 mg, 0.26 mmol) was dissolved in dichloromethane (2.5 ml) and subsequently treated with 4-nitrophenyl-chloroformate (96 mg, 0.45 mmol) and pyridine (0.038 ml, 0.47 mmol). After stirring for 7 h, the mixture was evaporated to dryness. Chromatography (silica, gradient of heptane/ethyl acetate 0 to 100%) afforded the title compound as white, viscous oil (82%). MS: m/e=596(M+H$^+$).

c) (2,2,3,3,3-Pentafluoro-propyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester

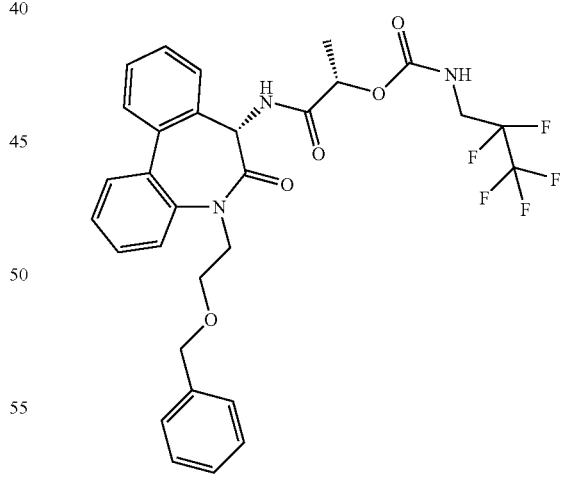

Chiral

Carbonic acid (S)-1-[(S)-5-(2-benzyloxy-ethyl)-6-oxo-6,7-dihydro-5H-dibenzo[b,d]azepin-7-ylcarbamoyl]-ethyl ester 4-nitro-phenyl ester (65 mg, 0.11 mmol) and 2,2,3,3,3-penta-fluoropropylamine (663 mg, 4.3 mmol) were stirred for 24 h at ambient temperature. After evaporation of all volatile components and chromatography on silica (gradient of heptane/ethyl acetate 0 to 80%), the title compound was obtained as white solid (>98%). MS: m/e=606(M+H$^+$).

EXAMPLE 6

N—[(S)-5-(2-Hydroxy-ethyl)-6-oxo-6,7-dihydro-5H-dibenzo[b,d]azepin-7-yl]-2,2-dimethyl-N'-(2,2,3,3,3-pentafluoro-propyl)-malonamide

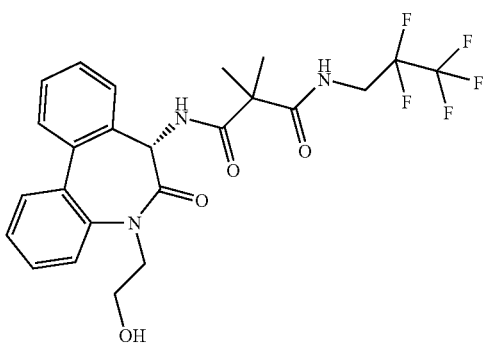

Chiral

Using N—[(S)-5-(2-benzyloxy-ethyl)-6-oxo-6,7-dihydro-5H-dibenzo[b,d]azepin-7-yl]-2,2-dimethyl-N-(2,2,3,3,3-pentafluoro-propyl)-malonamide, the title compound was prepared in the same manner as example 3 (>98%). White solid. MS: m/e=514(M+H$^+$).

EXAMPLE 7

N—[(S)-5-(2-Benzyloxy-ethyl)-6-oxo-6,7-dihydro-5H-dibenzo[b,d]azepin-7-yl]-N'-(2,2,3,3,3-pentafluoro-propyl)-malonamide a) N—[(S)-5-(2-Benzyloxy-ethyl)-6-oxo-6,7-dihydro-5H-dibenzo[b,d]azepin-7-yl]-malonamic acid ethyl ester

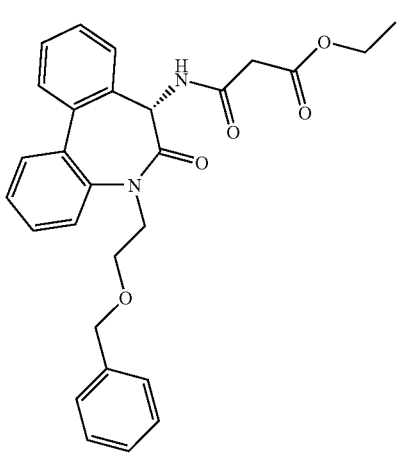

Chiral

Using (S)-7-amino-5-(2-benzyloxy-ethyl)-5H,7H-dibenzo[b,d]azepin-6-one and malonic acid monoethyl ester, the title compound was prepared in the same manner as described for example 1c. Colorless oil (>98%). MS: m/e=473(M+H$^+$).

b) N—[(S)-5-(2-Benzyloxy-ethyl)-6-oxo-6,7-dihydro-5H-dibenzo[b,d]azepin-7-yl]-malonamic acid

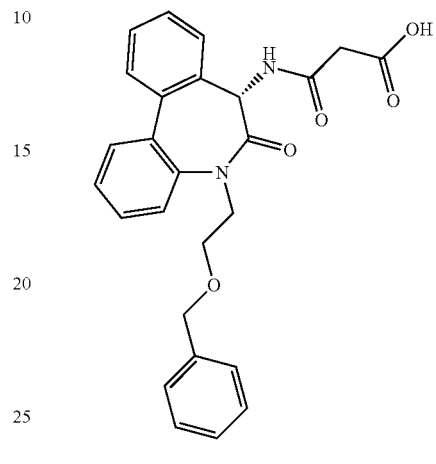

Chiral

Using N—[(S)-5-(2-benzyloxy-ethyl)-6-oxo-6,7-dihydro-5H-dibenzo[b,d]azepin-7-yl]-malonamic acid ethyl ester, the title compound was prepared in the same manner as example 4b. White, viscous oil (95%). MS: m/e=443(M−H$^+$).

c) N—[(S)-5-(2-Benzyloxy-ethyl)-6-oxo-6,7-dihydro-5H-dibenzo[b,d]azepin-7-yl]-N'-(2,2,3,3,3-pentafluoro-propyl)-malonamide

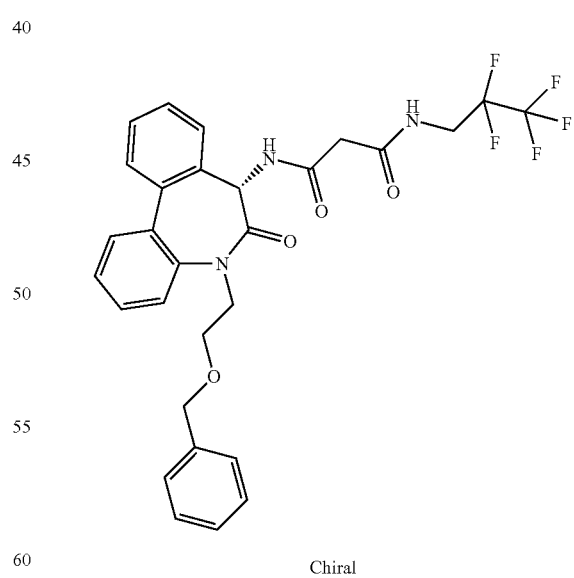

Chiral

Using N—[(S)-5-(2-benzyloxy-ethyl)-6-oxo-6,7-dihydro-5H-dibenzo[b,d]azepin-7-yl]-malonamic acid and N-(2,2,3,3,3-pentafluoro-propyl amine, the title compound was prepared in the same manner as example 1c (73%). White solid. MS: m/e=576(M+H$^+$).

EXAMPLE 8

(2,2,3,3,3-Pentafluoro-propyl)-carbamic acid (S)-1-[(S)-5-(2-hydroxy-ethyl)-6-oxo-6,7-dihydro-5H-dibenzo[b,d]azepin-7-ylcarbamoyl]-ethyl ester

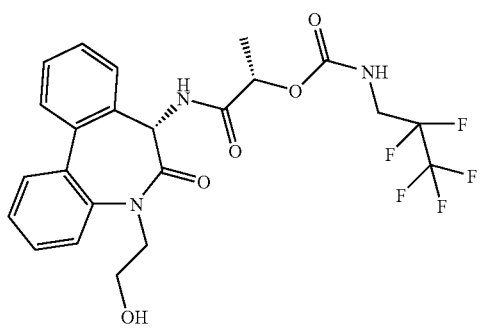

Chiral

Using (2,2,3,3,3-pentafluoro-propyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester, the title compound was prepared in the same manner as example 3 (96%). White solid. MS: m/e=516(M+H$^+$).

EXAMPLE 9

N—[(S)-5-(2-Hydroxy-ethyl)-6-oxo-6,7-dihydro-5H-dibenzo[b,d]azepin-7-yl]-N'-(2,2,3,3,3-pentafluoro-propyl)-malonamide

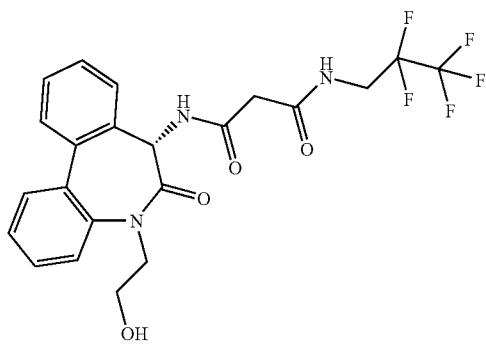

Chiral

Using N—[(S)-5-(2-benzyloxy-ethyl)-6-oxo-6,7-dihydro-5H-dibenzo[b,d]azepin-7-yl]-N'-(2,2,3,3,3-pentafluoro-propyl)-malonamide, the title compound was prepared in the same manner as example 3 (>98%%). White solid. MS: m/e=486(M+H$^+$).

EXAMPLE 10

N—[(S)-5-(2-Benzyloxy-ethyl)-6-oxo-6,7-dihydro-5H-dibenzo[b,d]azepin-7-yl]-2-methoxy-N'-(2,2,3,3,3-pentafluoro-propyl)-malonamide

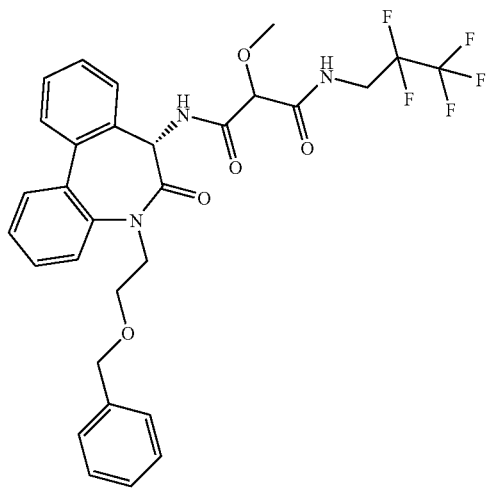

Using (S)-7-amino-5-(2-benzyloxy-ethyl)-5H,7H-dibenzo[b,d]azepin-6-one and 2-methoxy-N-(2,2,3,3,3-pentafluoro-propyl)-malonamic acid, the title compound was prepared in the same manner as example 1c (99%). White solid. MS: m/e=606(M+H$^+$).

EXAMPLE 11

N—[(S)-5-(2-Hydroxy-ethyl)-6-oxo-6,7-dihydro-5H-dibenzo[b,d]azepin-7-yl]-2-methoxy-N'-(2,2,3,3,3-pentafluoro-propyl)-malonamide

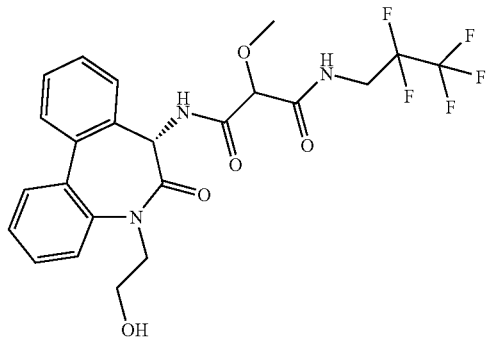

Using N—[(S)-5-(2-benzyloxy-ethyl)-6-oxo-6,7-dihydro-5H-dibenzo[b,d]azepin-7-yl]-2-methoxy-N'-(2,2,3,3,3-pentafluoro-propyl)-malonamide, the title compound was prepared in the same manner as example 3 (97%). White solid. MS: m/e=516(M+H$^+$).

EXAMPLE 12

N—[(S)-5-(2-Benzyloxy-ethyl)-6-oxo-6,7-dihydro-5H-dibenzo[b,d]azepin-7-yl]-2-hydroxy-2-methyl-N'-(2,2,3,3,3-pentafluoro-propyl)-malonamide a) N—[(S)-5-(2-Benzyloxy-ethyl)-6-oxo-6,7-dihydro-5H-dibenzo[b,d]azepin-7-yl]-2-hydroxy-2-methyl-malonamic acid ethyl ester

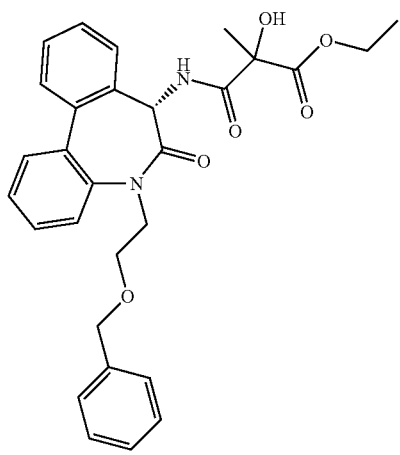

Using (S)-7-amino-5-(2-benzyloxy-ethyl)-5H,7H-dibenzo[b,d]azepin-6-one and 2-hydroxy-2-methyl-malonic acid monoethyl ester, the title compound was prepared in the same manner as described for example 1c. White solid (>98%). MS: m/e=503(M+H$^+$).

b) N—[(S)-5-(2-Benzyloxy-ethyl)-6-oxo-6,7-dihydro-5H-dibenzo[b,d]azepin-7-yl]-2-hydroxy-2-methyl-malonamic acid

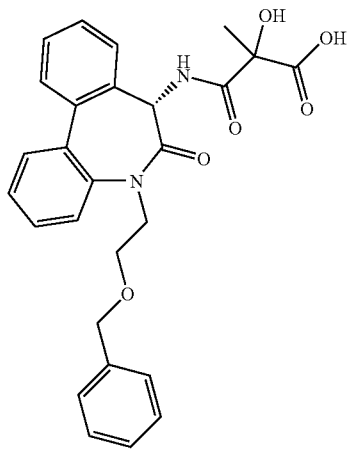

Using N—[(S)-5-(2-benzyloxy-ethyl)-6-oxo-6,7-dihydro-5H-dibenzo[b,d]azepin-7-yl]-2-hydroxy-2-methyl-malonamic acid ethyl ester, the title compound was prepared in the same manner as example 4b. White solid (90%). MS: m/e=473(M–H$^+$).

c) N—[(S)-5-(2-Benzyloxy-ethyl)-6-oxo-6,7-dihydro-5H-dibenzo[b,d]azepin-7-yl]-2-hydroxy-2-methyl-N'-(2,2,3,3,3-pentafluoro-propyl)-malonamide

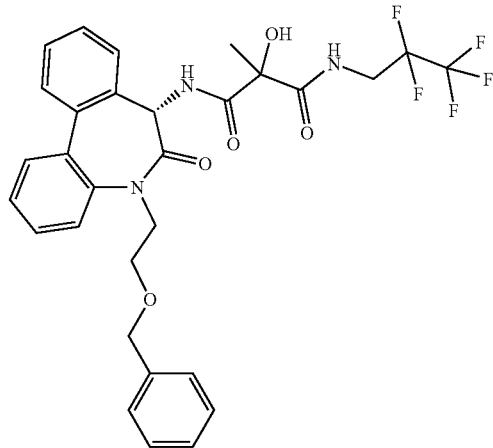

Using N—[(S)-5-(2-benzyloxy-ethyl)-6-oxo-6,7-dihydro-5H-dibenzo[b,d]azepin-7-yl]-2-hydroxy-2-methyl-malonamic acid and 2,2,3,3,3-pentafluoro-propylamine, the title compound was prepared in the same manner as example 1c (59%). White solid. MS: m/e=606(M+H$^+$).

EXAMPLE 13

N—[(S)-5-(2-Benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide a) N—[(S)-5-(2-Benzyloxy-ethyl)-6-oxo-6,7-dihydro-5H-dibenzo[b,d]azepin-7-yl]-2-fluoro-2-methyl-malonamic acid ethyl ester

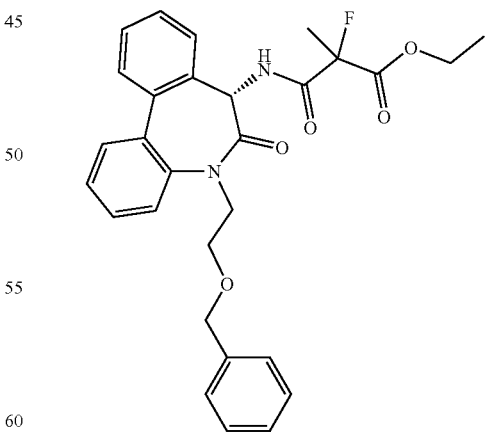

Using (S)-7-amino-5-(2-benzyloxy-ethyl)-5H,7H-dibenzo[b,d]azepin-6-one and 2-fluoro-2-methyl-malonic acid monoethyl ester, the title compound was prepared in the same manner as described for example 1c. Colorless oil (>98%). MS: m/e=505(M+H$^+$).

b) N—[(S)-5-(2-Benzyloxy-ethyl)-6-oxo-6,7-dihydro-5H-dibenzo[b,d]azepin-7-yl]-2-fluoro-2-methyl-malonamic acid

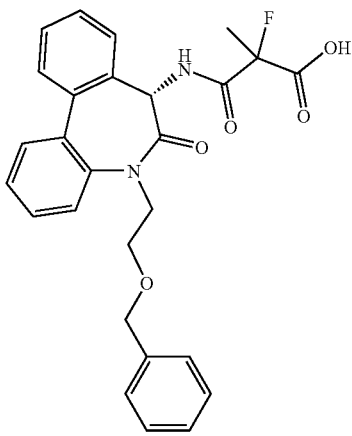

Using N—[(S)-5-(2-benzyloxy-ethyl)-6-oxo-6,7-dihydro-5H-dibenzo[b,d]azepin-7-yl]-2-fluoro-2-methyl-malonamic acid ethyl ester, the title compound was prepared in the same manner as example 4b. Colorless oil (85%). MS: m/e=4757 (M−H+).

c) N—[(S)-5-(2-Benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide

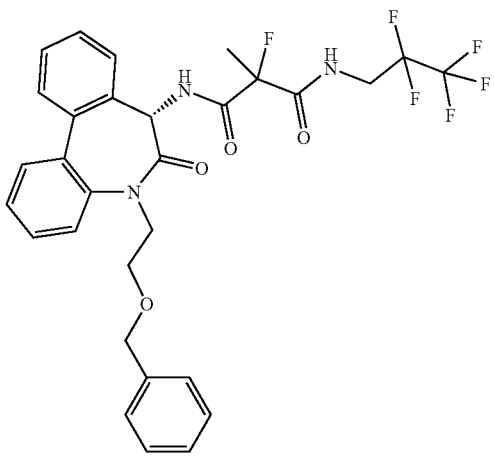

Using N—[(S)-5-(2-benzyloxy-ethyl)-6-oxo-6,7-dihydro-5H-dibenzo[b,d]azepin-7-yl]-2-fluoro-2-methyl-malonamic acid and 2,2,3,3,3-pentafluoropropylamine, the title compound was prepared in the same manner as described for example 1c. Whites solid. (64%). MS: m/e=608(M+H+).

EXAMPLE 14

N—[(S)-5-(2-Benzyloxy-ethyl)-6-oxo-6,7-[dihydro-5H-dibenzo[b,d]azepin-7-yl]-2-ethoxy-N'-(2,2,3,3,3-pentafluoro-propyl)-malonamide a) N—[(S)-5-(2-Benzyloxy-ethyl)-6-oxo-6,7-dihydro-5H-dibenzo[b,d]azepin-7-yl]-2-ethoxy-malonamic acid ethyl ester

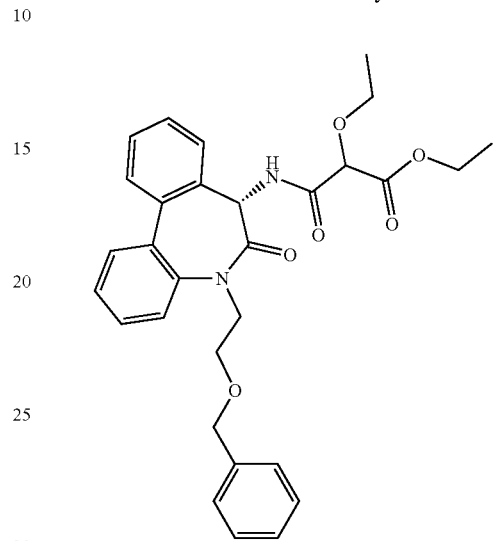

Using (S)-7-amino-5-(2-benzyloxy-ethyl)-5H,7H-dibenzo[b,d]azepin-6-one and 2-ethoxy-malonic acid monoethyl ester, the title compound was prepared in the same manner as described for example 1c. Colorless oil (94%). MS: m/e=517(M+H+).

b) N—[(S)-5-(2-Benzyloxy-ethyl)-6-oxo-6,7-dihydro-5H-dibenzo[b,d]azepin-7-yl]-2-ethoxy-malonamic acid

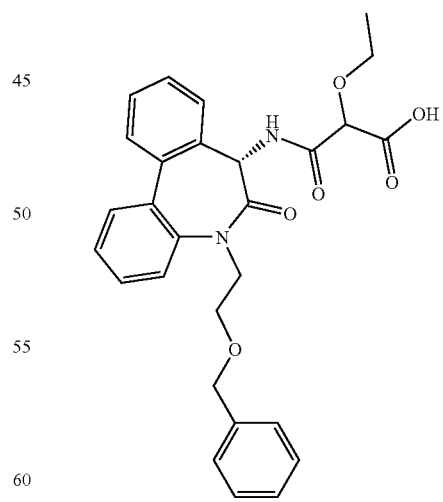

Using N—[(S)-5-(2-benzyloxy-ethyl)-6-oxo-6,7-dihydro-5H-dibenzo[b,d]azepin-7-yl]-2-ethoxy-malonamic acid ethyl ester, the title compound was prepared in the same manner as example 4b. Colorless oil (88%). MS: m/e=487 (M−H+).

c) N—[(S)-5-(2-Benzyloxy-ethyl)-6-oxo-6,7-dihydro-5H-dibenzo[b,d]azepin-7-yl]-2-ethoxy-N'-(2,2,3,3,3-pentafluoro-propyl)-malonamide

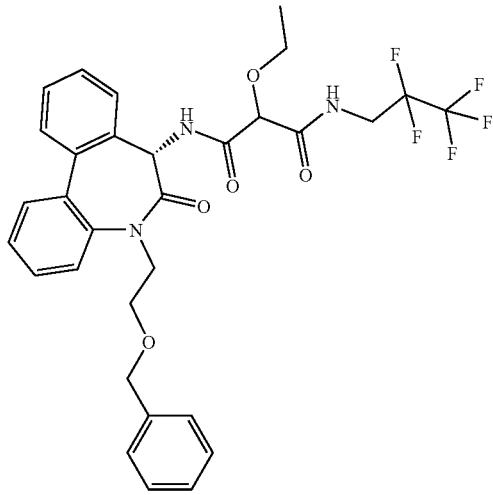

Using N—[(S)-5-(2-benzyloxy-ethyl)-6-oxo-6,7-dihydro-5H-dibenzo[b,d]azepin-7-yl]-2-ethoxy-malonamic acid and 2,2,3,3,3-pentafluoropropylamine, the title compound was prepared in the same manner as described for example 1c. White solid. (82%). MS: m/e=620(M+H+).

EXAMPLE 15

2-Hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide

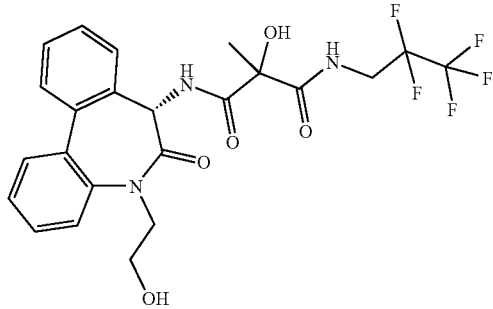

Using N—[(S)-5-(2-benzyloxy-ethyl)-6-oxo-6,7-dihydro-5H-dibenzo[b,d]azepin-7-yl]-2-hydroxy-2-methyl-N'-(2,2,3,3,3-pentafluoro-propyl)-malonamide, the title compound was prepared in the same manner as described for example 3. White solid (>98%). MS: m/e=516(M+H+).

EXAMPLE 16

2-Fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide

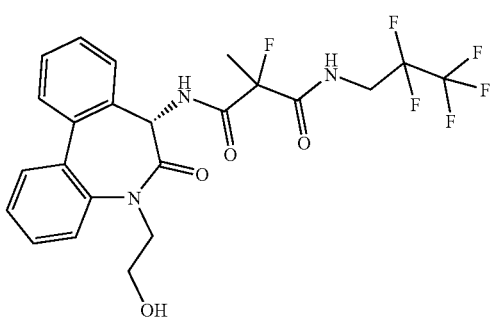

Using N—[(S)-5-(2-benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide and 2,2,3,3,3-pentafluoropropylamine, the title compound was prepared in the same manner as described for example 3. White solid (94%). MS: m/e=518(M+H+).

EXAMPLE 17

2-Ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide

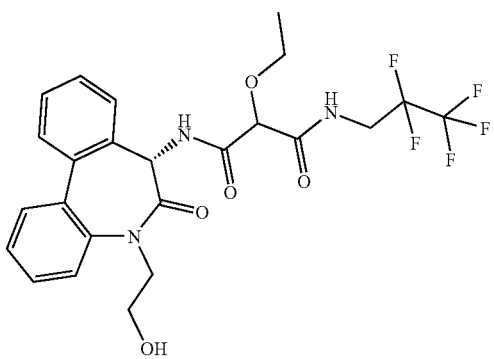

Using N—[(S)-5-(2-benzyloxy-ethyl)-6-oxo-6,7-dihydro-5H-dibenzo[b,d]azepin-7-yl]-2-ethoxy-N'-(2,2,3,3,3-pentafluoro-propyl)-malonamide and 2,2,3,3,3-pentafluoropropylamine, the title compound was prepared in the same manner as described for example 3. White solid (83%). MS: m/e=530(M+H+).

EXAMPLE 18

(S or R)-2-Ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, epimer A

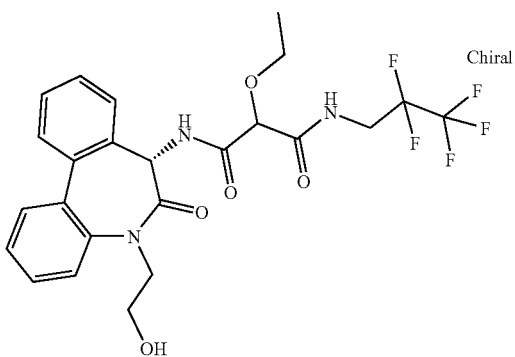

Separation of 2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide (HPLC on Chiralpak AD, eluent heptane/ethyl acetate 3/7) afforded the title compound as first eluting material with negative rotation. Off-white, viscous oil (39%). MS: m/e=530(M+H$^+$).

EXAMPLE 19

[R or S]2-Ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, epimer B

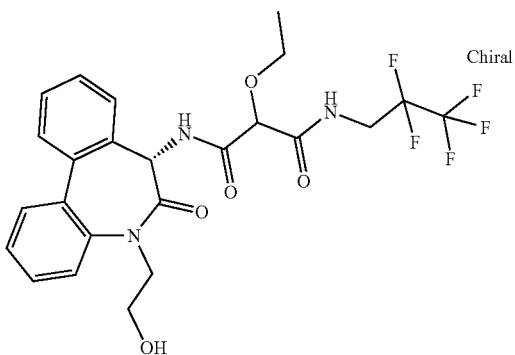

Separation of 2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide (HPLC on Chiralpak AD, eluent heptane/ethyl acetate 3/7) afforded the title compound as second eluting material with negative rotation. Off-white, viscous oil (52%). MS: m/e=530(M+H$^+$).

EXAMPLE 20

2-Hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide, epimer A

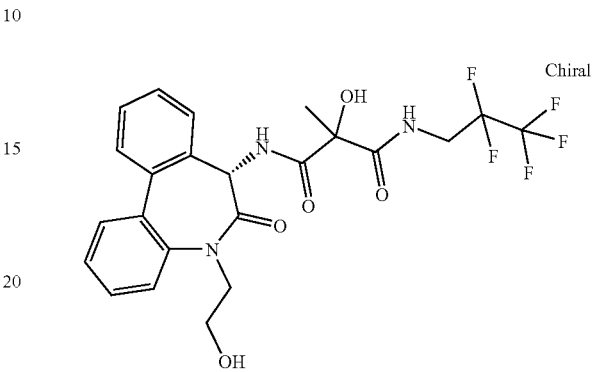

Separation of 2-hydroxy-N—[(S)-5-(2-hydroxy-ethyl)-6-oxo-6,7-dihydro-5H-dibenzo[b,d]azepin-7-yl]-2-methyl-N$^1$-(2,2,3,3,3-pentafluoro-propyl)-malonamide on chiral HPLC (Chrialpak OD) afforded the title compound as first eluting material with negative rotation (36%). White solid. MS: m/e=516(M+H$^+$).

EXAMPLE 21

2-Hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide epimer B

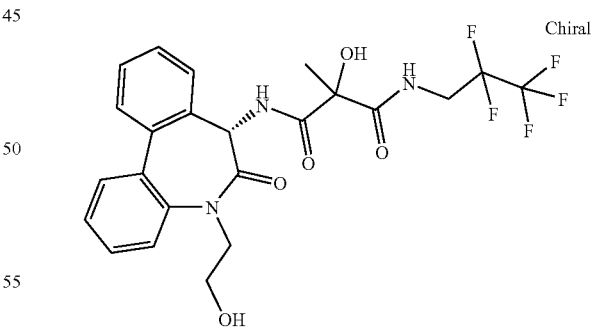

Separation of 2-hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide on chiral HPLC (Chrialpak OD) afforded the title compound as second eluting material with negative rotation (38%). White solid. MS: m/e=516(M+H$^+$).

EXAMPLE 22

(R)—N—[(S)-5-(2-Benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide a) (S)—N—[(S)-5-(2-Benzyloxy-ethyl)-6-oxo-6,7-dihydro-5H-dibenzo[b,d]azepin-7-yl]-2-fluoro-2-methyl-malonamic acid ethyl ester

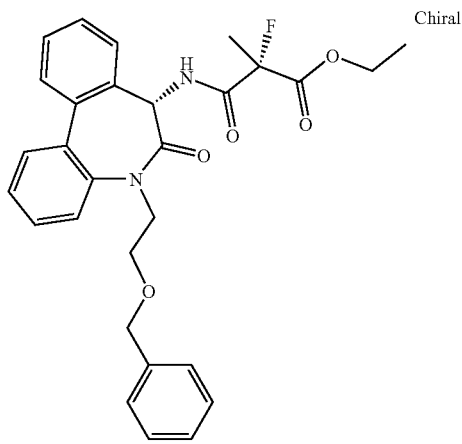

Using (S)-7-amino-5-(2-benzyloxy-ethyl)-5H,7H-dibenzo[b,d]azepin-6-one and (S)-2-fluoro-2-methyl-malonic acid monoethyl ester, the title compound was prepared in the same manner as described for example 1c. Light yellow oil (>98%). MS: m/e=505(M+H$^+$).

b) (S)—N—[(S)-5-(2-Benzyloxy-ethyl)-6-oxo-6,7-dihydro-5H-dibenzo[b,d]azepin-7-yl]-2-fluoro-2-methyl-malonamic acid

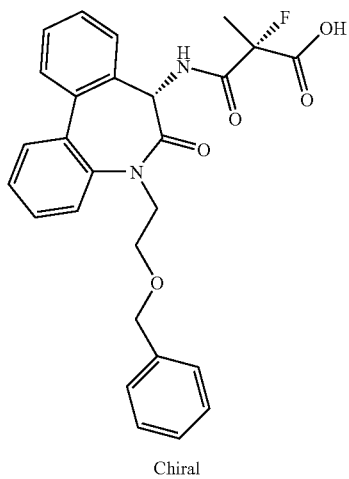

Using (S)—N—[(S)-5-(2-benzyloxy-ethyl)-6-oxo-6,7-dihydro-5H-dibenzo[b,d]azepin-7-yl]-2-fluoro-2-methyl-malonamic acid ethyl ester, the title compound was prepared in the same manner as described for example 4b. White solid. (71%). MS: m/e=475(M−H$^+$).

c) (R)—N—(S)-5-(2-Benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide

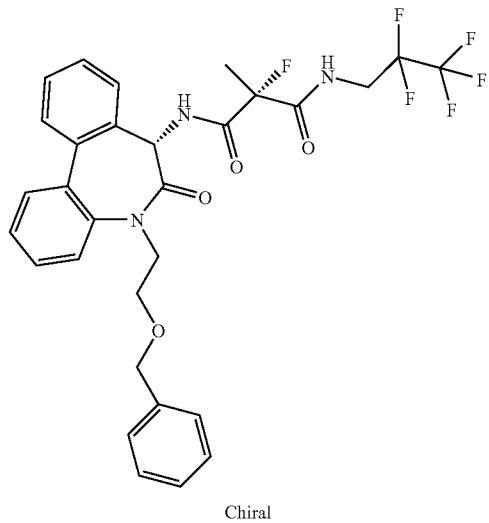

Using (S)—N—[(S)-5-(2-benzyloxy-ethyl)-6-oxo-6,7-dihydro-5H-dibenzo[b,d]azepin-7-yl]-2-fluoro-2-methyl-malonamic acid and 2,2,3,3,3-pentafluoropropylamine, the title compound was prepared in the same manner as described for example 1c. White solid (74%). MS: m/e=608(M+H$^+$).

EXAMPLE 23

(S)—N—[(S)-5-(2-Benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide a) (R)—N—[(S)-5-(2-Benzyloxy-ethyl)-6-oxo-6,7-dihydro-5H-dibenzo[b,d]azepin-7-yl]-2-fluoro-2-methyl-malonamic acid ethyl ester

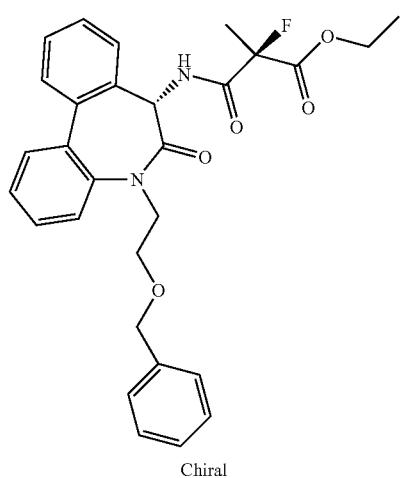

Using (S)-7-amino-5-(2-benzyloxy-ethyl)-5H,7H-dibenzo[b,d]azepin-6-one and (R)-2-fluoro-2-methyl-malonic acid monoethyl ester, the title compound was prepared in the same manner as described for example 1c. Light yellow oil (96%). MS: m/e=505(M+H⁺).

b) (R)—N—[(S)-5-(2-Benzyloxy-ethyl)-6-oxo-6,7-dihydro-5H-dibenzo[b,d]azepin-7-yl]-2-fluoro-2-methyl-malonamic acid

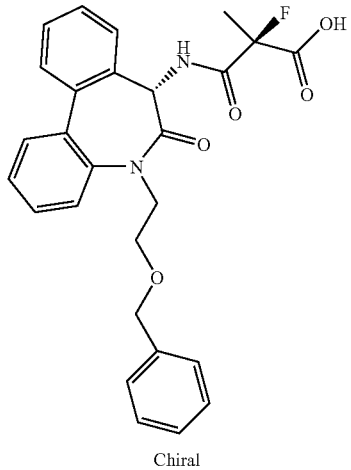

Chiral

Using (R)—N—[(S)-5-(2-benzyloxy-ethyl)-6-oxo-6,7-dihydro-5H-dibenzo[b,d]azepin-7-yl]-2-fluoro-2-methyl-malonamic acid ethyl ester, the title compound was prepared in the same manner as described for example 4b. White solid. (83%). MS: m/e=475(M−H⁺).

c) (S)—N—[(S)-5-(2-Benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide

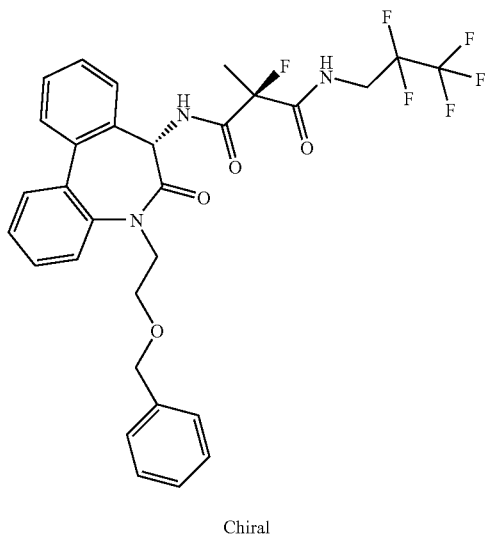

Chiral

Using (R)—N—[(S)-5-(2-benzyloxy-ethyl)-6-oxo-6,7-dihydro-5H-dibenzo[b,d]azepin-7-yl]-2-fluoro-2-methyl-malonamic acid and 2,2,3,3,3-pentafluoropropylamine, the title compound was prepared in the same manner as described for example 1c. White solid (63%). MS: m/e=608(M+H⁺).

EXAMPLE 24

N—[(S)-5-(2-Methoxy-ethyl)-6-oxo-6,7-dihydro-5H-dibenzo[b,d]azepin-7-yl]-N'-(2,2,3,3,3-pentafluoro-propyl)-malonamide a) [(S)-5-(2-Methoxy-ethyl)-6-oxo-6,7-dihydro-5H-dibenzo[b,d]azepin-5-yl]-carbamic acid tert-butyl ester

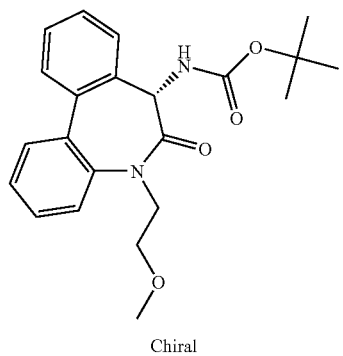

Chiral

Using ((S)-6-oxo-6,7-dihydro-5H-dibenzo[b,d]azepin-7-yl)-carbamic acid tert-butyl ester and 1-bromo-2-methoxy-ethane, the title compound was prepared in the same manner as example 1a. Pink solid (90%). MS: m/e=383(M+H⁺).

b) (S)-7-Amino-5-(2-methoxy-ethyl)-5H,7H-dibenzo[b,d]azepin-6-one

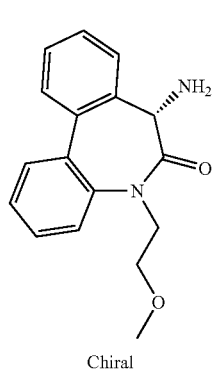

Chiral

[(S)-5-(2-methoxy-ethyl)-6-oxo-6,7-dihydro-5H-dibenzo[b,d]azepin-5-yl]-carbamic acid tert-butyl ester (637 mg, 1.7 mmol) and trifluoroacetic acid (10 equivalents) were dissolved in dichloromethane (10 ml) and stirred for 3 h at ambient temperature. Work-up and isolation as described in example 1b afforded the title compound as colorless, viscous oil (99%). MS: m/e=283(M+H⁺).

c) N—[(S)-5-(2-Methoxy-ethyl)-6-oxo-6,7-dihydro-5H-dibenzo[b,d]azepin-7-yl]-malonamic acid ethyl ester

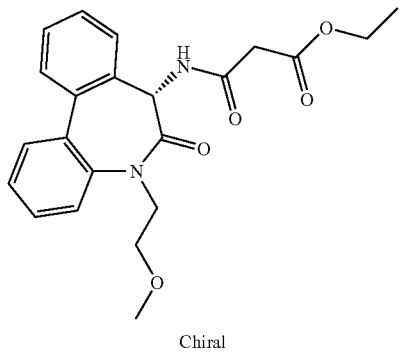
Chiral

Using (S)-7-Amino-5-(2-methoxy-ethyl)-5H,7H-dibenzo[b,d]azepin-6-one and malonic acid monoethyl ester, the title compound was prepared in the same manner as described for example 1c. Colorless, viscous oil (>98%). MS: m/e=397 (M+H$^+$).

d) N—[(S)-5-(2-Methoxy-ethyl)-6-oxo-6,7-dihydro-5H-dibenzo[b,d]azepin-7-yl]-malonamic acid

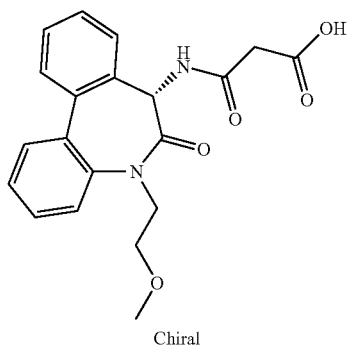
Chiral

Using (R)—N—[(S)-5-(2-benzyloxy-ethyl)-6-oxo-6,7-dihydro-5H-dibenzo[b,d]azepin-7-yl]-2-malonamic acid ethyl ester, the title compound was prepared in the same manner as described for example 4b. White solid. (85%). MS: m/e=367 (M−H$^+$).

e) N—[(S)-5-(2-Methoxy-ethyl)-6-oxo-6,7-dihydro-5H-dibenzo[b,d]azepin-7-yl]-N'-(2,2,3,3,3-pentafluoro-propyl)-malonamide

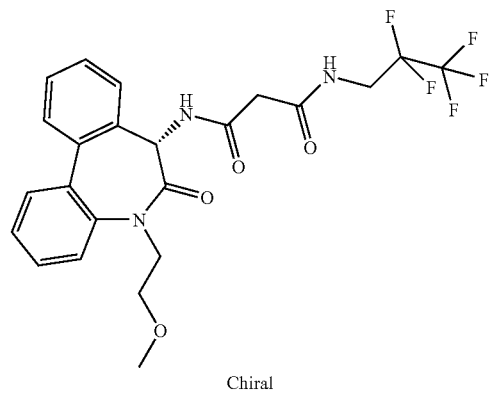
Chiral

Using N—[(S)-5-(2-methoxy-ethyl)-6-oxo-6,7-dihydro-5H-dibenzo[b,d]azepin-7-yl]-malonamic acid and 2,2,3,3,3-pentafluoropropylamine, the title compound was prepared in the same manner as described for example 1c. White solid (80%). MS: m/e=500(M+H$^+$).

EXAMPLE 25

(2,2,3,3,3-Pentafluoro-propyl)-carbamic acid (S)-1-[(S)-5-(2-methoxy-ethyl)-6-oxo-6,7-dihydro-5H-dibenzo[b,d]azepin-7-ylcarbamoyl]-ethyl ester a) (S)-2-Hydroxy-N—[(S)-5-(2-methoxy-ethyl)-6-oxo-6,7-dihydro-5H-dibenzo[b,d]azepin-7-yl]-propionamide

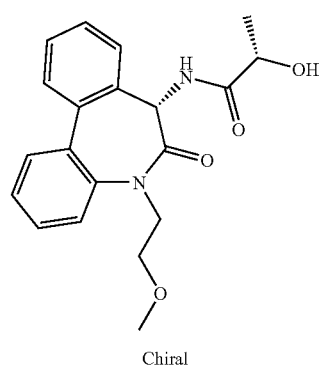
Chiral

Using (S)-7-amino-5-(2-methoxy-ethyl)-5H,7H-dibenzo[b,d]azepin-6-one and L-(+)-lactic acid, the title compound was prepared in the same manner as described for example 5a. Colourless, viscous oil (>98%). MS: m/e=355(M+H$^+$).

b) Carbonic acid (S)-1-1[(S)-5-(2-methoxy-ethyl)-6-oxo-6,7-dihydro-5H-dibenzo[b,d]azepin-7-ylcarbamoyl]-ethyl ester 4-nitro-phenyl ester

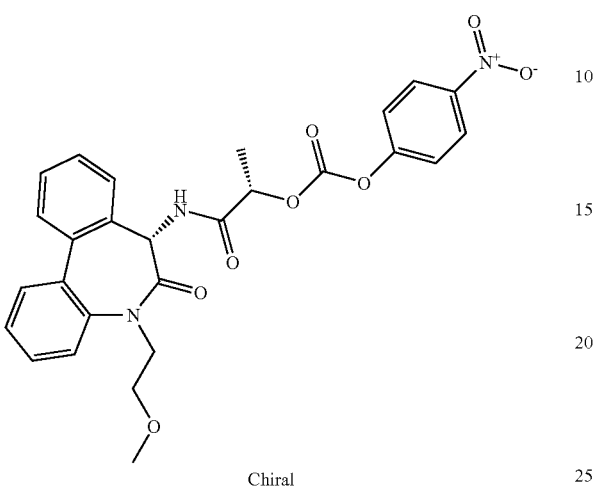

Chiral

Using (S)-2-hydroxy-N—[(S)-5-(2-methoxy-ethyl)-6-oxo-6,7-dihydro-5H-dibenzo[b,d]azepin-7-yl]-propionamide, the title compound was prepared in the same manner as described for example 5b. White solid (89%). MS: m/e=520 (M+H$^+$).

c) (2,2,3,3,3-Pentafluoro-propyl)-carbamic acid (S)-1-[(S)-5-(2-methoxy-ethyl)-6-oxo-6,7-dihydro-5H-dibenzo[b,d]azepin-7-ylcarbamoyl]-ethyl ester

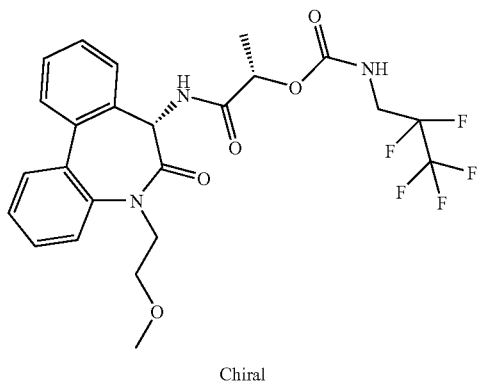

Chiral

Using carbonic acid (S)-1-[(S)-5-(2-methoxy-ethyl)-6-oxo-6,7-dihydro-5H-dibenzo[b,d]azepin-7-ylcarbamoyl]-ethyl ester 4-nitro-phenyl ester and 2,2,3,3,3-pentafluoropropylamine, the title compound was prepared in the same manner as described for example 5c. White solid (49%). MS: m/e=530(M+H$^+$).

EXAMPLE 26

(R)-2-Fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide

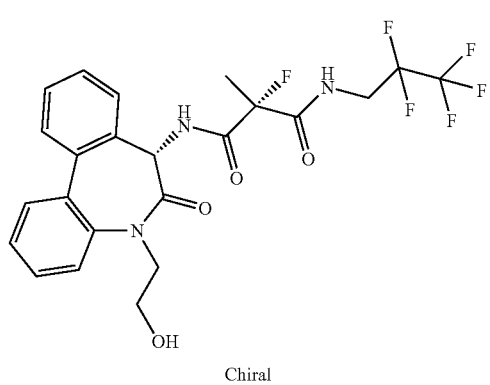

Chiral

Using (R)—N—[(S)-5-(2-benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide, the title compound was prepared in the same manner as example 3 (>98%). White solid. MS: m/e=518(M+H$^+$).

EXAMPLE 27

(S)-2-Fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide

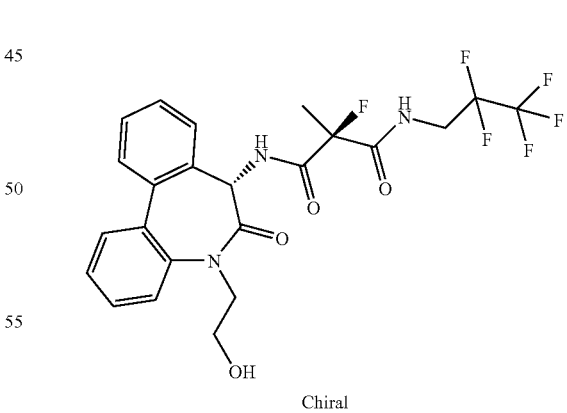

Chiral

Using (S)—N—[(S)-5-(2-benzyloxy-ethyl)-6-oxo-6,7-dihydro-5H-dibenzo[b,d]azepin-7-yl]-2-fluoro-2-methyl-N'-(2,2,3,3,3-pentafluoro-propyl)-malonamide, the title compound was prepared in the same manner as example 3 (96%). White solid. MS: m/e=518(M+H$^+$).

EXAMPLE 28

N—[(S)-5-(2-Benzyloxy-ethyl)-6-oxo-6,7-dihydro-5H-dibenzo[b,d]azepin-7-yl]-N'-(3,3,3-trifluoro-propyl)-malonamide

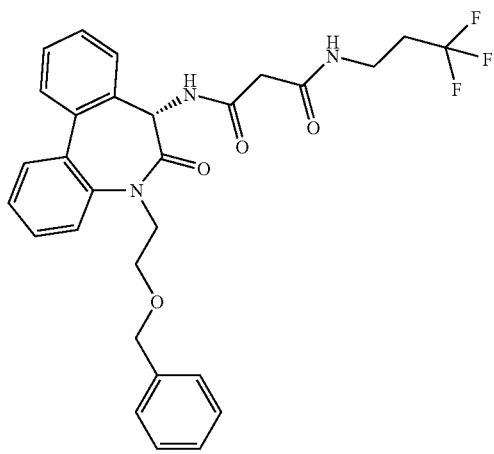

Using N—[(S)-5-(2-benzyloxy-ethyl)-6-oxo-6,7-dihydro-5H-dibenzo[b,d]azepin-7-yl]-malonamic acid and 3,3,3-trifluoropropylamine, the title compound was prepared in the same manner as described for example 1c. Colorless, waxy solid (90%). MS: m/e=540(M+H$^+$).

EXAMPLE 29

N—[(S)-5-(2-Benzyloxy-ethyl)-6-oxo-6,7-dihydro-5H-dibenzo[b,d]azepin-7-yl]-N'-(3,3,4,4,4-pentafluoro-butyl)-malonamide

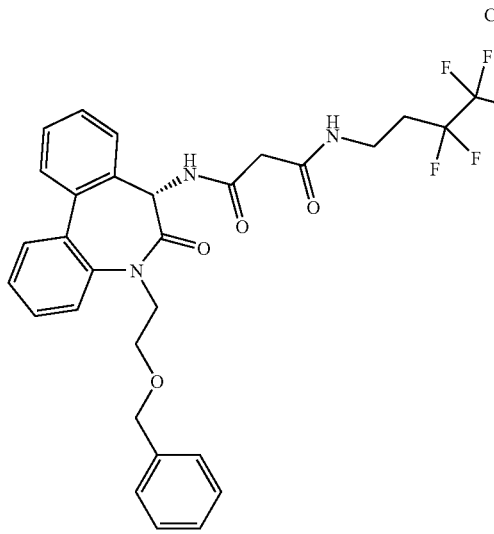

Using N—[(S)-5-(2-benzyloxy-ethyl)-6-oxo-6,7-dihydro-5H-dibenzo[b,d]azepin-7-yl]-malonamic acid and ,3,3,4,4,4-pentafluorobutylamine, the title compound was prepared in the same manner as described for example 1c. Colorless, waxy solid (98%). MS: m/e=590(M+H$^+$).

EXAMPLE 30

N—[(S)-5-(2-Hydroxy-ethyl)-6-oxo-6,7-dihydro-5H-dibenzo[b,d]azepin-7-yl]-N'-(3,3,3-trifluoro-propyl)-malonamide

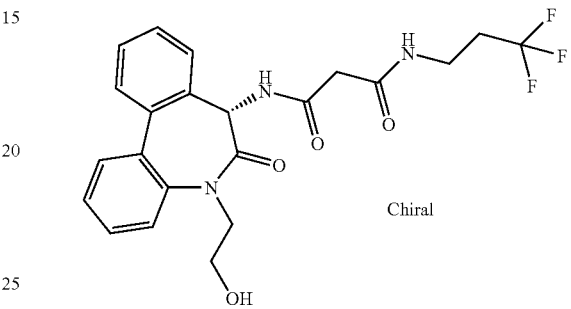

Using N—[(S)-5-(2-Benzyloxy-ethyl)-6-oxo-6,7-dihydro-5H-dibenzo[b,d]azepin-7-yl]-N'-(3,3,3-trifluoro-propyl)-malonamide, the title compound was prepared in the same manner as example 3 (85%). White solid. MS: m/e=450 (M+H$^+$).

EXAMPLE 31

N—[(S)-5-(2-Hydroxy-ethyl)-6-oxo-6,7-dihydro-5H-dibenzo[b,d]azepin-7-yl]-N'-(3,3,4,4,4-pentafluoro-butyl)-malonamide

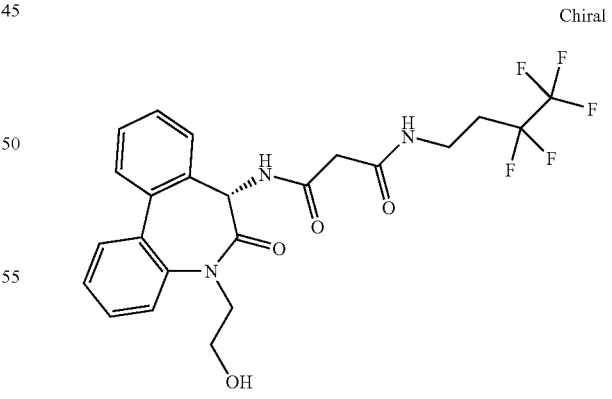

Using N—[(S)-5-(2-Benzyloxy-ethyl)-6-oxo-6,7-dihydro-5H-dibenzo[b,d]azepin-7-yl]-N'-(3,3,4,4,4-pentafluoro-butyl)-malonamide, the title compound was prepared in the same manner as example 3 (>98%). Light brown solid. MS: m/e=500(M+H$^+$).

EXAMPLE 32

(S)-2-Fluoro-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide a) (R)-2-Fluoro-N—[(S)-5-(2-methoxy-ethyl)-6-oxo-6,7-dihydro-5H-dibenzo[b,d]azepin-7-yl]-2-methyl-malonamic acid ethyl ester

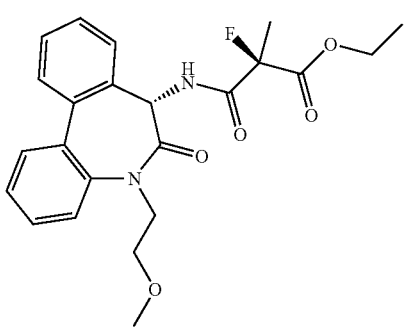

Using (S)-7-amino-5-(2-methoxy-ethyl)-5H,7H-dibenzo[b,d]azepin-6-one and (R)-2-fluoro-2-methyl-malonic acid monoethyl ester, the title compound was prepared in the same manner as described for example 1c. Colorless oil (59%). MS: m/e=429(M+H$^+$).

b) (R)-2-Fluoro-N—[(S)-5-(2-methoxy-ethyl)-6-oxo-6,7-dihydro-5H-dibenzo[b,d]azepin-7-yl]-2-methyl-malonamic acid

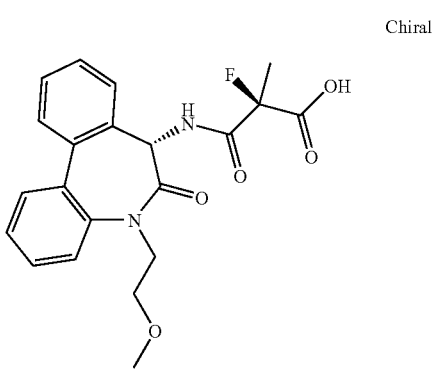

Using (R)-2-fluoro-N—[(S)-5-(2-methoxy-ethyl)-6-oxo-6,7-dihydro-5H-dibenzo[b,d]azepin-7-yl]-2-methyl-malonamic acid ethyl ester, the title compound was prepared in the same manner as described for example 4b. White semi-solid. (>98%). MS: m/e=399(M−H$^+$).

c) (S)-2-Fluoro-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide

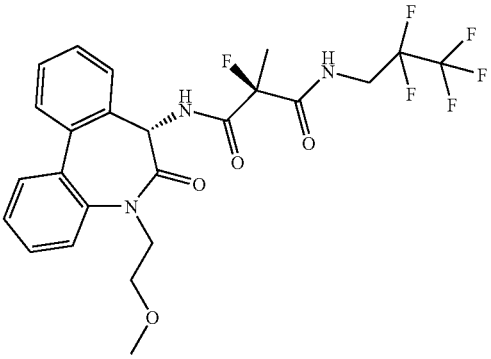

Using (R)-2-fluoro-N—[(S)-5-(2-methoxy-ethyl)-6-oxo-6,7-dihydro-5H-dibenzo[b,d]azepin-7-yl]-2-methyl-malonamic acid and 2,2,3,3,3-pentafluoropropylamine, the title compound was prepared in the same manner as described for example 1c. White solid (69%). MS: m/e=532(M+H$^+$).

EXAMPLE 33

(R)-2-Fluoro-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide a) (S)-2-Fluoro-N—[(S)-5-(2-methoxy-ethyl)-6-oxo-6,7-dihydro-5H-dibenzo[b,d]azepin-7-yl]-2-methyl-malonamic acid ethyl ester

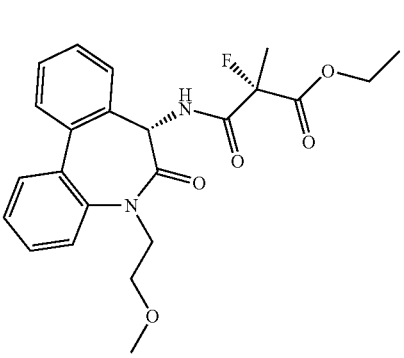

Using (S)-7-amino-5-(2-methoxy-ethyl)-5H,7H-dibenzo[b,d]azepin-6-one and (S)-2-fluoro-2-methyl-malonic acid monoethyl ester, the title compound was prepared in the same manner as described for example 1c. Colorless oil (50%). MS: m/e=429(M+H$^+$).

b) (S)-2-Fluoro-N—[(S)-5-(2-methoxy-ethyl)-6-oxo-6,7-dihydro-5H-dibenzo[b,d]azepin-7-yl]-2-methyl-malonamic acid

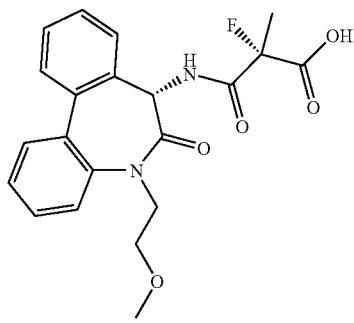
Chiral

Using (S)-2-fluoro-N—[(S)-5-(2-methoxy-ethyl)-6-oxo-6,7-dihydro-5H-dibenzo[b,d]azepin-7-yl]-2-methyl-malonamic acid ethyl ester, the title compound was prepared in the same manner as described for example 4b. White solid. (>98%). MS: m/e=399(M−H+).

c) (R)-2-Fluoro-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide

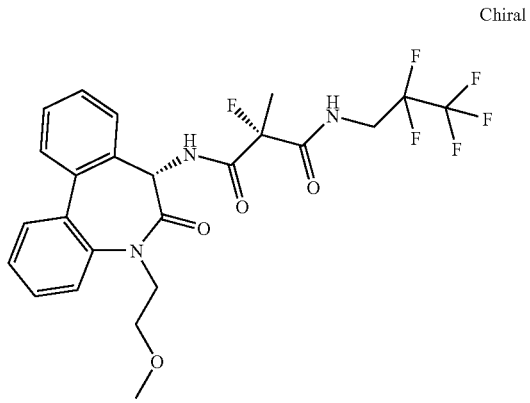
Chiral

Using (S)-2-fluoro-N—[(S)-5-(2-methoxy-ethyl)-6-oxo-6,7-dihydro-5H-dibenzo[b,d]azepin-7-yl]-2-methyl-malonamic acid and 2,2,3,3,3-pentafluoropropylamine, the title compound was prepared in the same manner as described for example 1c. White solid (71%). MS: m/e=532(M+H+).

EXAMPLE 34

2-Hydroxy-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide a) 2-Hydroxy-N—[(S)-5-(2-methoxy-ethyl)-6-oxo-6,7-dihydro-5H-dibenzo[b,d]azepin-7-yl]-2-methyl-malonamic acid ethyl ester

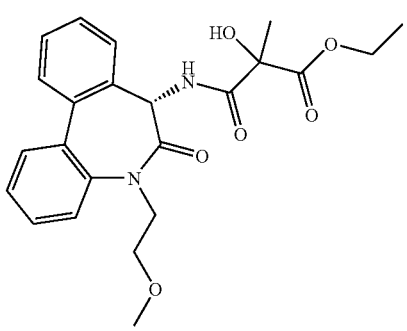

Using (S)-7-amino-5-(2-methoxy-ethyl)-5H,7H-dibenzo[b,d]azepin-6-one and 2-hydroxy-2-methyl-malonic acid monoethyl ester, the title compound was prepared in the same manner as described for example 1c. Colorless oil. (66%). MS: m/e=426(M+H+).

b) 2-Hydroxy-N—[(S)-5-(2-methoxy-ethyl)-6-oxo-6,7-dihydro-5H-dibenzo[b,d]azepin-7-yl]-2-methyl-malonamic acid

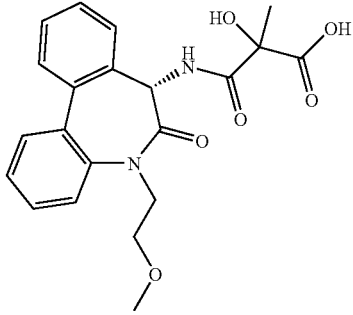

Using 2-hydroxy-N—[(S)-5-(2-methoxy-ethyl)-6-oxo-6,7-dihydro-5H-dibenzo[b,d]azepin-7-yl]-2-methyl-malonamic acid ethyl ester, the title compound was prepared in the same manner as described for example 4b. White solid. (>98%). MS: m/e=397(M−H+).

c) 2-Hydroxy-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide

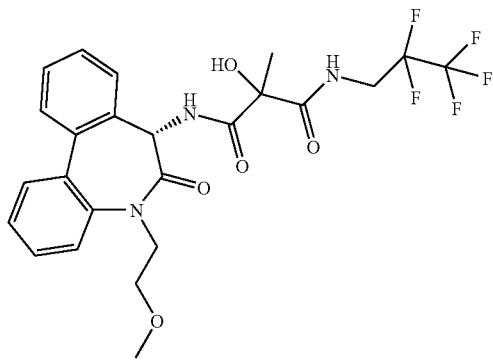

Using 2-hydroxy-N—[(S)-5-(2-methoxy-ethyl)-6-oxo-6,7-dihydro-5H-dibenzo[b,d]azepin-7-yl]-2-methyl-malonamic acid and 2,2,3,3,3-pentafluoropropylamine, the title compound was prepared in the same manner as described for example 1c. White solid (78%). MS: m/e=530(M+H+).

EXAMPLE 35

(3,3,3-Trifluoro-propyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester

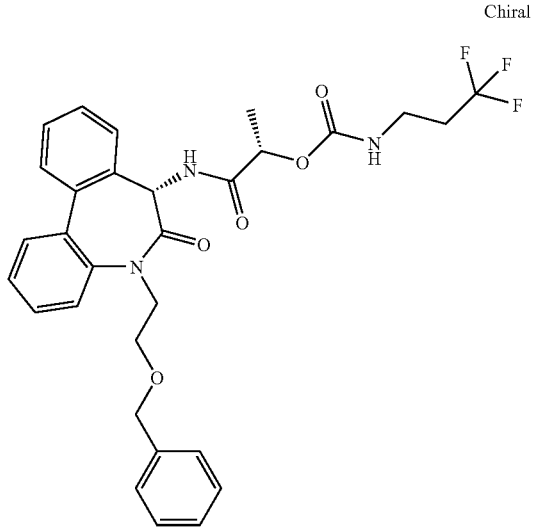

Using carbonic acid (S)-1-[(S)-5-(2-benzyloxy-ethyl)-6-oxo-6,7-dihydro-5H-dibenzo[b,d]azepin-7-ylcarbamoyl]-ethyl ester 4-nitro-phenyl ester and 3,3,3-trifluoropropylamine, the title compound was prepared in the same manner as described for example 5c. Colorless, waxy solid (94%). MS: m/e=570(M+H+).

EXAMPLE 36

(3,3,4,4,4-Pentafluoro-butyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester

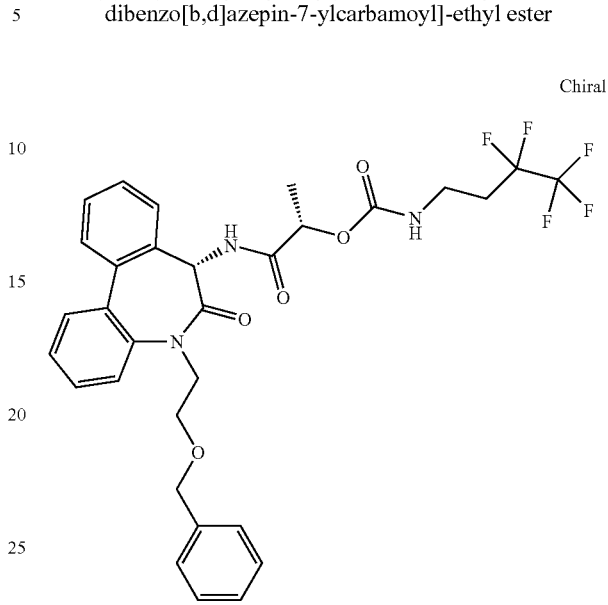

Using carbonic acid (S)-1-[(S)-5-(2-benzyloxy-ethyl)-6-oxo-6,7-dihydro-5H-dibenzo[b,d]azepin-7-ylcarbamoyl]-ethyl ester 4-nitro-phenyl ester and 3,3,4,4,4-pentafluorobutylamine, the title compound was prepared in the same manner as described for example 5c. White solid (97%). MS: m/e=620(M+H+).

EXAMPLE 37

(2,2,2-Trifluoro-ethyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester

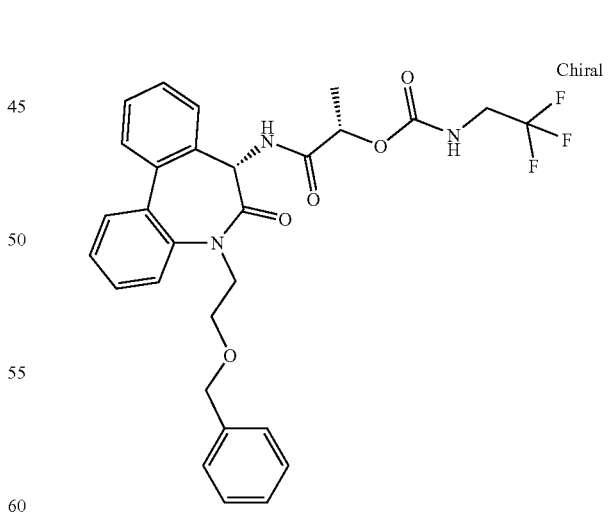

Using carbonic acid (S)-1-[(S)-5-(2-benzyloxy-ethyl)-6-oxo-6,7-dihydro-5H-dibenzo[b,d]azepin-7-ylcarbamoyl]-ethyl ester 4-nitro-phenyl ester and 2,2,2-trifluoroethylamine, the title compound was prepared in the same manner as described for example 5c. Colorless, waxy solid (94%). MS: m/e=556(M+H+).

EXAMPLE 38

(3,3,4,4,4-Pentafluoro-butyl)-carbamic acid (S)-1-[(S)-5-(2-hydroxy-ethyl)-6-oxo-6,7-dihydro-5H-dibenzo[b,d]azepin-7-ylcarbamoyl]-ethyl ester

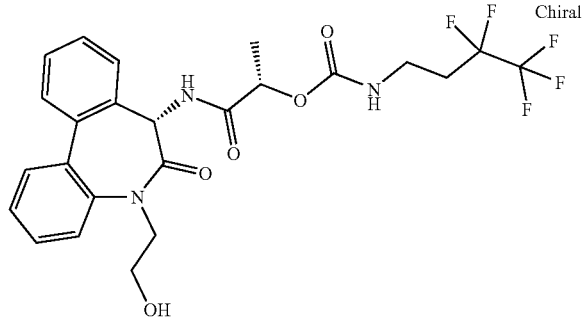

Using (3,3,4,4,4-pentafluoro-butyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester, the title compound was prepared in the same manner as example 3 (70%). Yellow, crystals, mp 181-184° C. MS: m/e=530(M+H$^+$).

EXAMPLE 39

(3,3,3-Trifluoro-propyl)-carbamic acid (S)-1-[(S)-5-(2-hydroxy-ethyl)-6-oxo-6,7-dihydro-5H-dibenzo[b,d]azepin-7-ylcarbamoyl]-ethyl ester

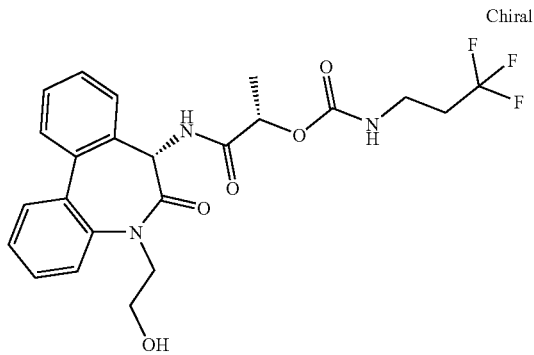

Using (3,3,3-trifluoro-propyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester, the title compound was prepared in the same manner as example 3 (72%). Colorless, waxy solid. MS: m/e=480(M+H$^+$).

EXAMPLE 40

(R)—N—[(S)-5-(2-Benzyloxy-ethyl)-6-oxo-6,7-dihydro-5H-dibenzo[b,d]azepin-7-yl]-2-fluoro-2-methyl-N'-(3,3,4,4,4-pentafluoro-butyl)-malonamide

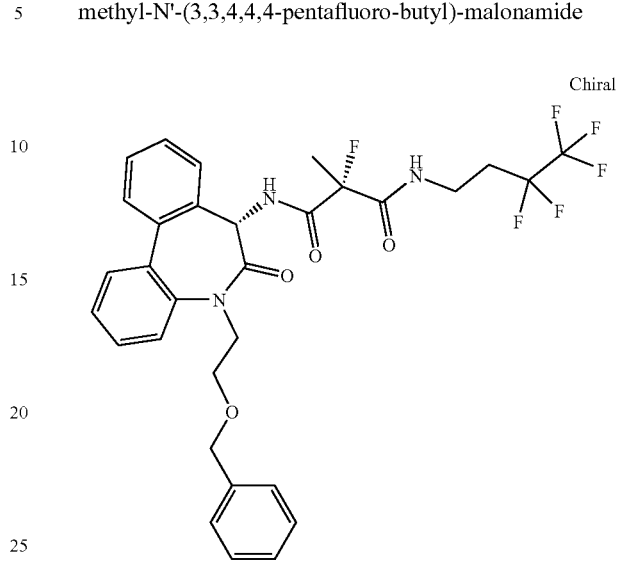

Using (S)—N—[(S)-5-(2-benzyloxy-ethyl)-6-oxo-6,7-dihydro-5H-dibenzo[b,d]azepin-7-yl]-2-fluoro-2-methyl-malonamic acid and 3,3,4,4,4-pentafluoro-butylamine, the title compound was prepared in the same manner as described for example 1c. White solid (85%). MS: m/e=622(M+H$^+$).

EXAMPLE 41

(2-Fluoro-ethyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester

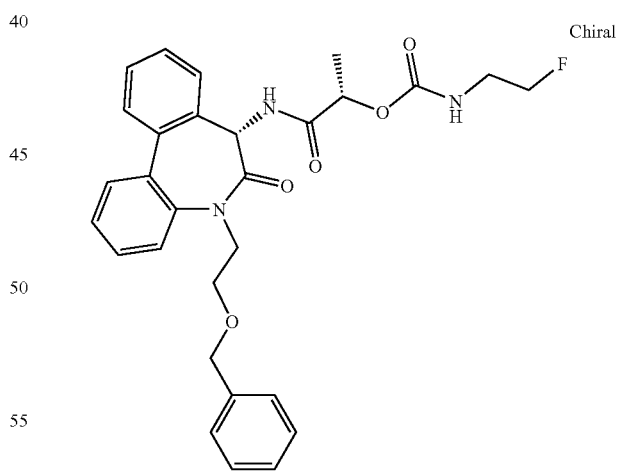

Carbonic acid (S)-1-[(S)-5-(2-benzyloxy-ethyl)-6-oxo-6,7-dihydro-5H-dibenzo[b,d]azepin-7-ylcarbamoyl]-ethyl ester 4-nitro-phenyl ester (80 mg, 0.13 mmol), 2-fluoroethylamine hydrochloride (40 mg, 0.40 mmol) and pyridine (2 ml) were stirred in a sealed tube for 18 h at ambient temperature. After evaporation of the volatile components under reduced pressure, the residue was taken up in water/ethyl acetate, the phases separated and the organic layer extracted 5-times with saturated aqueous sodium carbonate, twice with 10% citric acid and once with saturated aqueous sodium chloride. After drying over magnesium sulphate and evaporation of the solvent, the title compound is obtained as white solid (>98%). MS: n/e=520(M+H⁺).

EXAMPLE 42

(R)-2-Fluoro-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide

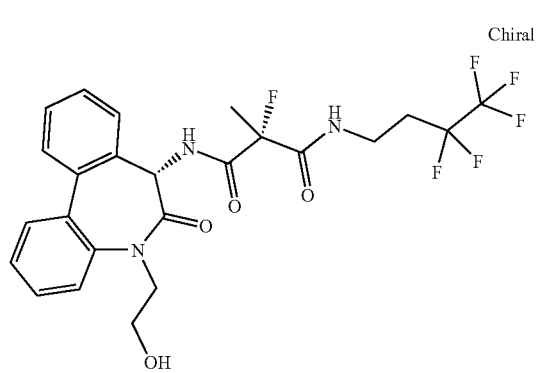

Using (R)—N—[(S)-5-(2-benzyloxy-ethyl)-6-oxo-6,7-dihydro-5H-dibenzo[b,d]azepin-7-yl]-2-fluoro-2-methyl-N'-(3,3,4,4,4-pentafluoro-butyl)-malonamide, the title compound was prepared in the same manner as example 3 Final chromatography on silica (heptane/ethyl acetate gradient from 20 to 80%) afforded the title compound as white solid (56%). MS: m/e=532(M+H⁺).

EXAMPLE 43

(S)—N—[(S)-5-(2-Benzyloxy-ethyl)-6-oxo-6,7-dihydro-5H-dibenzo[b,d]azepin-7-yl]-2-fluoro-2-methyl-N'-(2,2,2-trifluoro-ethyl)-malonamide

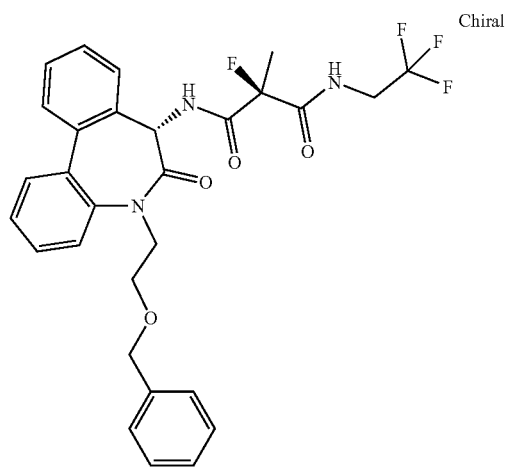

Using (R)—N—[(S)-5-(2-benzyloxy-ethyl)-6-oxo-6,7-dihydro-5H-dibenzo[b,d]azepin-7-yl]-2-fluoro-2-methyl-malonamic acid and 2,2,2-trifluoro-ethylamine, the title compound was prepared in the same manner as described for example 1c. Final chromatography on silica (heptane/ethyl acetate gradient from 5 to 100%) afforded the title compound as white solid (58%). MS: m/e=558(M+H⁺).

EXAMPLE 44

(S)—N—[(S)-5-(2-Benzyloxy-ethyl)-6-oxo-6,7-dihydro-5H-dibenzo[b,d]azepin-7-yl]-2-fluoro-2-methyl-N'-(3,3,4,4,4-pentafluoro-butyl)-malonamide

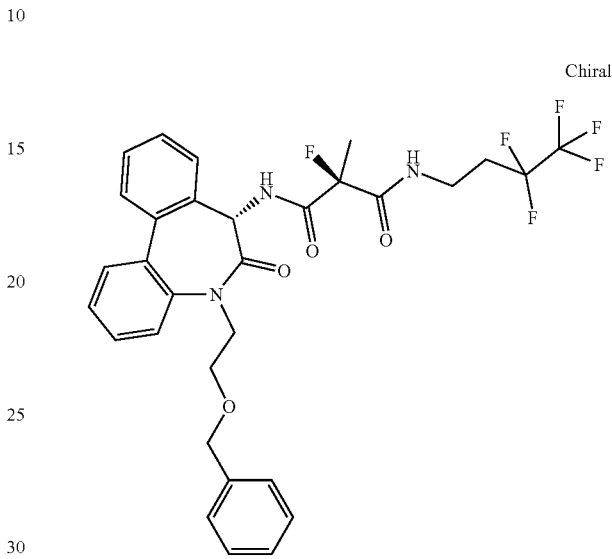

Using (R)—N—[(S)-5-(2-benzyloxy-ethyl)-6-oxo-6,7-dihydro-5H-dibenzo[b,d]azepin-7-yl]-2-fluoro-2-methyl-malonamic acid and 3,3,4,4,4-pentafluoro-butylamine, the title compound was prepared in the same manner as described for example 1c. White solid (68%). MS: m/e=622(M+H⁺).

EXAMPLE 45

2-Hydroxy-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide, epimer A

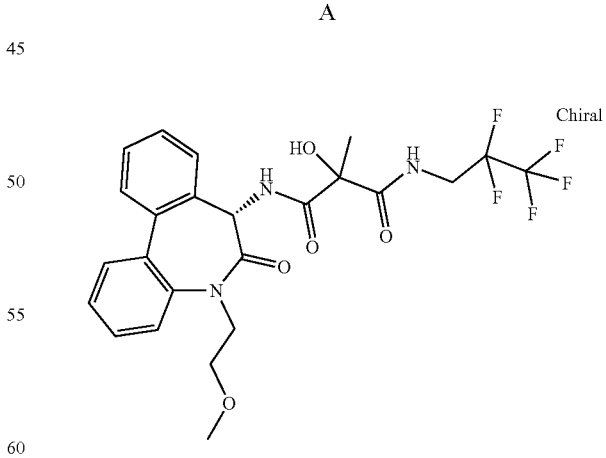

Separation of 2-hydroxy-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide by chiral HPLC (Chiralpak AD) afforded the title compound as first eluting material with negative rotation. White solid (33%). MS: m/e=530(M+H⁺).

EXAMPLE 46

2-Hydroxy-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide, epimer B

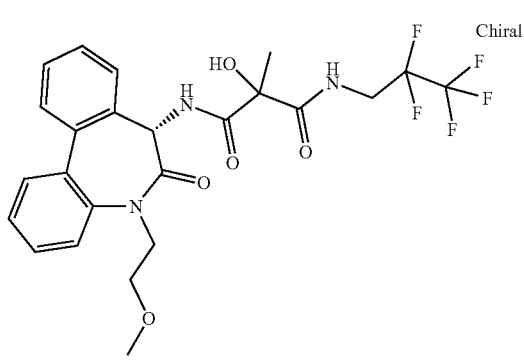

Separation of 2-hydroxy-N—[(S)-5-(2-methoxy-ethyl)-6-oxo-6,7-dihydro-5H-dibenzo[b,d]azepin-7-yl]-2-methyl-N'-(2,2,3,3,3-pentafluoro-propyl)-malonamide by chiral HPLC (Chiralpak AD) afforded the title compound as second eluting material with negative rotation. White solid (39%). MS: m/e=530(M+H$^+$).

EXAMPLE 47

(2-Fluoro-ethyl)-carbamic acid (S)-1-[(S)-5-(2-hydroxy-ethyl)-6-oxo-6,7-dihydro-5H-dibenzo[b,d]azepin-7-ylcarbamoyl]-ethyl ester

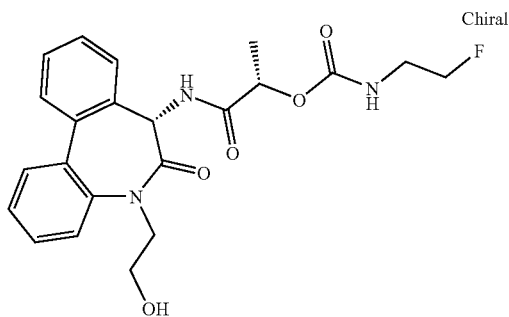

Using (2-fluoro-ethyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester, the title compound was prepared in the same manner as example 3 (>98%). Light yellow solid. MS: m/e=430(M+H$^+$).

EXAMPLE 48

(2,2,2-Trifluoro-ethyl)-carbamic acid (S)-1-[(S)-5-(2-hydroxy-ethyl)-6-oxo-6,7-dihydro-5H-dibenzo[b,d]azepin-7-ylcarbamoyl]-ethyl ester

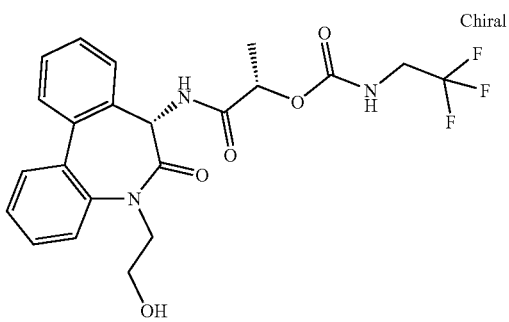

Using (2,2,2-trifluoro-ethyl)-carbamic acid (S)-1-[(S)-5-(2-benzyloxy-ethyl)-6-oxo-6,7-dihydro-5H-dibenzo[b,d]azepin-7-ylcarbamoyl]-ethyl ester, the title compound was prepared in the same manner as example 3. Final chromatography (silica, gradient of ethyl acetate in heptane 5-90%) afforded the title compound as white solid (70%). MS: m/e=466(M+H$^+$).

EXAMPLE 49

(S)-2-Fluoro-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide Using (S)—N—[(S)-5-(2-benzyloxy-ethyl)-6-oxo-6,7-dihydro-5H-dibenzo[b,d]azepin-7-yl]-2-fluoro-2-methyl-N'-(2,2,2-trifluoro-ethyl)-malonamide, the title compound was prepared in the same manner as example 3 (>98%%). Light yellow solid. MS: m/e=468(M+H$^+$).

EXAMPLE 50

(S)-2-Fluoro-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide

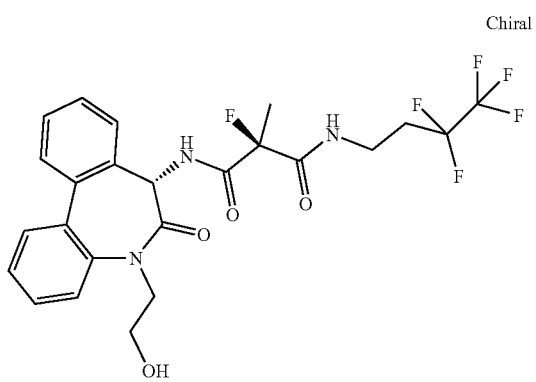

Using (S)—N—[(S)-5-(2-benzyloxy-ethyl)-6-oxo-6,7-dihydro-5H-dibenzo[b,d]azepin-7-yl]-2-fluoro-2-methyl-N'-(3,3,4,4,4-pentafluoro-butyl)-malonamide, the title compound was prepared in the same manner as example 3 (>98%%). White solid. MS: m/e=532(M+H$^+$).

EXAMPLE 51

(R)—N—[(S)-5-(2-Benzyloxy-ethyl)-6-oxo-6,7-dihydro-5H-dibenzo[b,d]azepin-7-yl]-2-fluoro-2-methyl-N'-(3,3,3-trifluoro-propyl)-malonamide

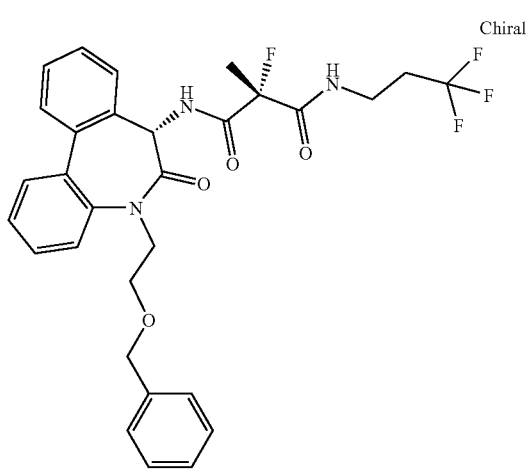

Using (S)—N—[(S)-5-(2-benzyloxy-ethyl)-6-oxo-6,7-dihydro-5H-dibenzo[b,d]azepin-7-yl]-2-fluoro-2-methyl-malonamic acid and 3,3,3-trifluoropropylamine, the title compound was prepared in the same manner as described for example 1c. Colorless, viscous oil (72%). MS: m/e=572(M+H$^+$).

EXAMPLE 52

(R)—N—[(S)-5-(2-Benzyloxy-ethyl)-6-oxo-6,7-dihydro-5H-dibenzo[b,d]azepin-7-yl]-2-fluoro-2-methyl-N'-(2,2,2-trifluoro-ethyl)-malonamide

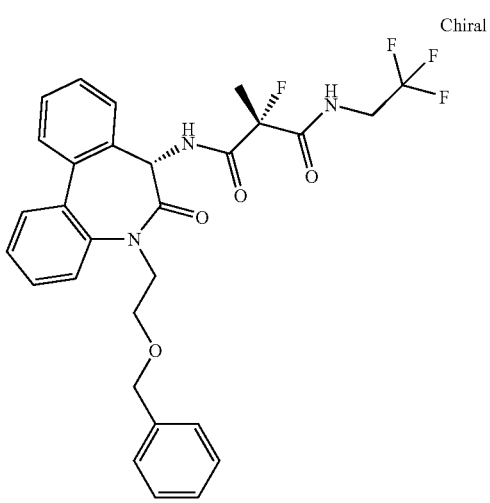

Using (S)—N—[(S)-5-(2-benzyloxy-ethyl)-6-oxo-6,7-dihydro-5H-dibenzo[b,d]azepin-7-yl]-2-fluoro-2-methyl-malonamic acid and 2,2,2-trifluoroethylamine, the title compound was prepared in the same manner as described for example 1c. Colorless, viscous oil (73%). MS: m/e=558(M+H$^+$).

EXAMPLE 53

(R)-2-Fluoro-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide

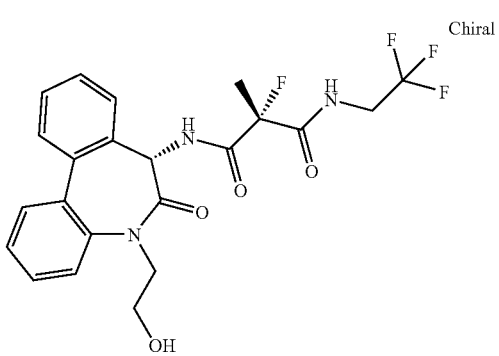

Using (R)—N—[(S)-5-(2-benzyloxy-ethyl)-6-oxo-6,7-dihydro-5H-dibenzo[b,d]azepin-7-yl]-2-fluoro-2-methyl-N-(2,2,2-trifluoro-ethyl)-malonamide, the title compound prepared in the same manner as example 3 (91%). White solid. MS: m/e=468(M+H$^+$).

EXAMPLE 54

(R)-2-Fluoro-N—[(S)-5-(2-hydroxy-ethyl)-6-oxo-6,7-dihydro-5H-dibenzo[b,d]azepin-7-yl]-2-methyl-N-(3,3,3-trifluoro-propyl)-malonamide

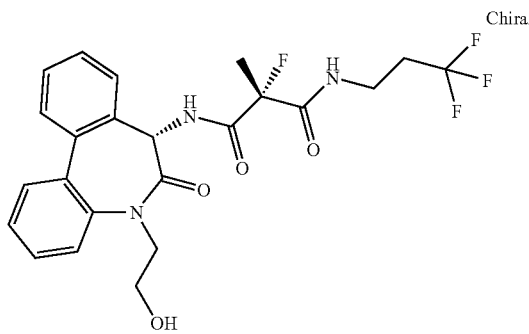

Using (R)—N—[(S)-5-(2-benzyloxy-ethyl)-6-oxo-6,7-dihydro-5H-dibenzo[b,d]azepin-7-yl]-2-fluoro-2-methyl-N'-(3,3,3-trifluoro-propyl)-malonamide, the title compound was prepared in the same manner as example 3 (95%). Off-white solid. MS: m/e=482(M+H$^+$).

EXAMPLE 55

N—[(S)-5-(2-Benzyloxy-ethyl)-6-oxo-6,7-dihydro-5H-dibenzo[b,d]azepin-7-yl]-2-hydroxy-2-methyl-N'-(3,3,4,4-pentafluoro-butyl)-malonamide

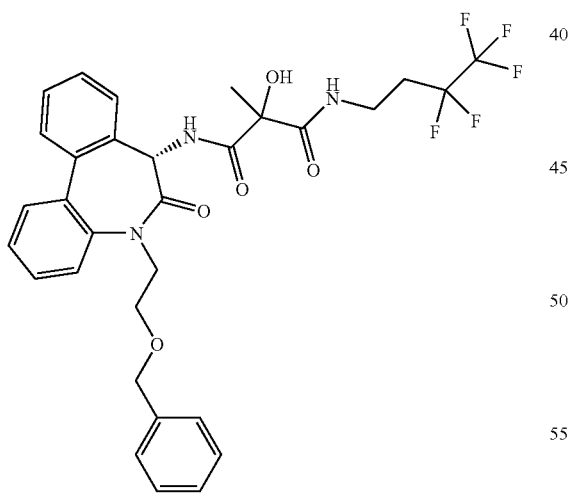

Using N—[(S)-5-(2-benzyloxy-ethyl)-6-oxo-6,7-dihydro-5H-dibenzo[b,d]azepin-7-yl]-2-hydroxy-2-methyl-malonamic acid and 3,3,4,4,4-pentafluorobutylamine, the title compound was prepared in the same manner as described for example 1c. Light yellow, viscous oil (88%). MS: m/e=620 (M+H$^+$).

EXAMPLE 56

2-Hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide

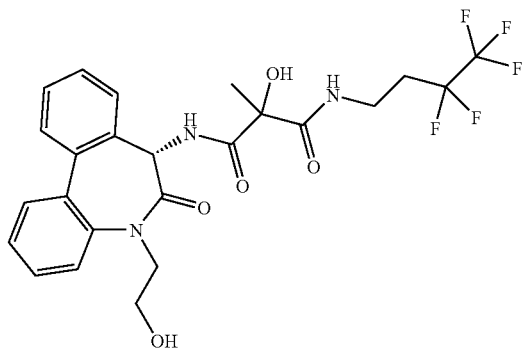

Using N—[(S)-5-(2-Benzyloxy-ethyl)-6-oxo-6,7-dihydro-5H-dibenzo[b,d]azepin-7-yl]-2-hydroxy-2-methyl-N'-(3,3,4,4,4-pentafluoro-butyl)-malonamide, the title compound was prepared in the same manner as example 3 (92%). Off-white solid. MS: m/e=530(M+H$^+$).

EXAMPLE 57

(R)—N—[(S)-5-(2-Benzyloxy-ethyl)-6-oxo-6,7-dihydro-5H-dibenzo[b,d]azepin-7-yl]-2-hydroxy-2-methyl-N'-(2,2,2-trifluoro-ethyl)-malonamide

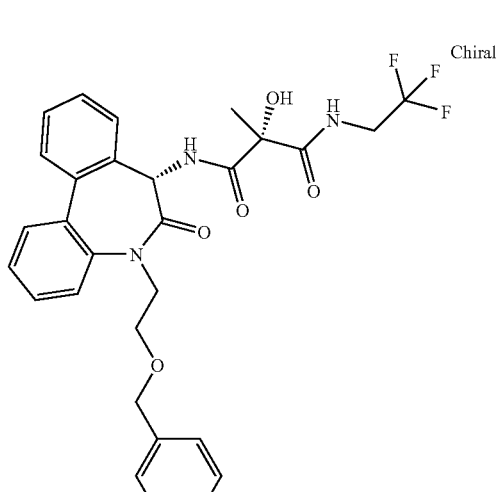

Using (S)-7-amino-5-(2-benzyloxy-ethyl)-5H,7H-dibenzo[b,d]azepin-6-one and (R)-2-hydroxy-2-methyl-N-(2,2,2-trifluoro-ethyl)-malonamic acid, the title compound was prepared in the same manner as described for example 1c. Colorless, amorphous solid (96%). MS: m/e=556(M+H$^+$).

EXAMPLE 58

(S)—N—[(S)-5-(2-Benzyloxy-ethyl)-6-oxo-6,7-dihydro-5H-dibenzo[b,d]azepin-7-yl]-2-hydroxy-2-methyl-N'-(2,2,2-trifluoro-ethyl)-malonamide

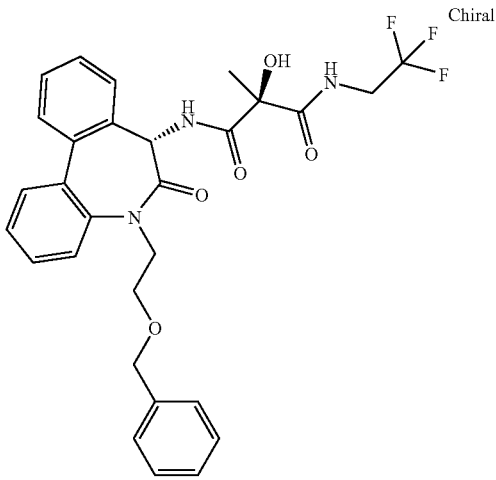

Using (S)-7-amino-5-(2-benzyloxy-ethyl)-5H,7H-dibenzo[b,d]azepin-6-one and (S)-2-hydroxy-2-methyl-N-(2,2,2-trifluoro-ethyl)-malonamic acid, the title compound was prepared in the same manner as described for example 1c. Colorless, amorphous solid (91%). MS: m/e=556(M+H$^+$).

EXAMPLE 59

(R)-2-Hydroxy-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide

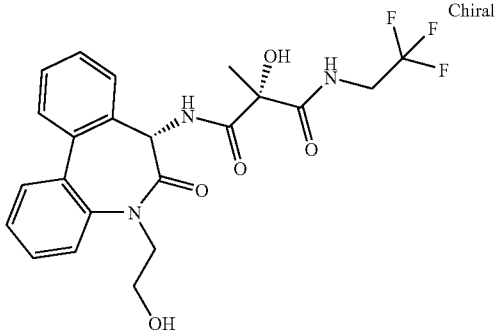

Using (R)—N—[(S)-5-(2-benzyloxy-ethyl)-6-oxo-6,7-dihydro-5H-dibenzo[b,d]azepin-7-yl]-2-hydroxy-2-methyl-N'-(2,2,2-trifluoro-ethyl)-malonamide, the title compound was prepared in the same manner as example 3 (>98%). White solid. MS: m/e=466(M+H$^+$).

EXAMPLE 60

(S)-2-Hydroxy-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide

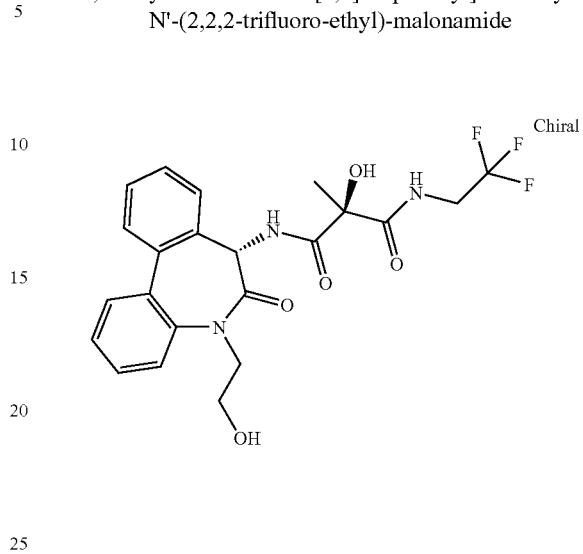

Using (S)—N—[(S)-5-(2-benzyloxy-ethyl)-6-oxo-6,7-dihydro-5H-dibenzo[b,d]azepin-7-yl]-2-hydroxy-2-methyl-N'-(2,2,2-trifluoro-ethyl)-malonamide, the title compound was prepared in the same manner as example 3 (>98%). White solid. MS: m/e=466(M+H$^+$).

EXAMPLE 61

(R or S)-2-Hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, epimer A

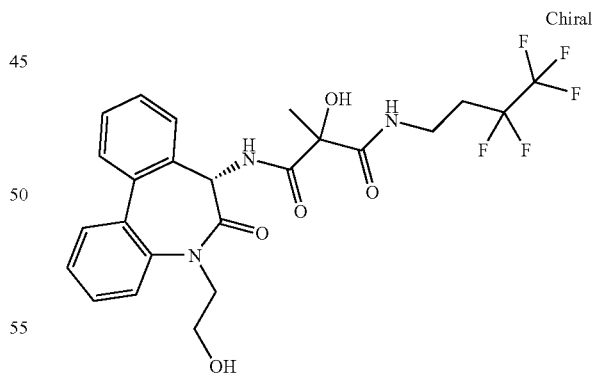

Separation of 2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide (HPLC on Chiralpak AD, eluent 20% ethanol in heptane) afforded the title compound as first eluting material with negative rotation. White solid (65% of th.). MS: m/e=530(M+H$^+$).

EXAMPLE 62

(S or R)-2-Hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, epimer B

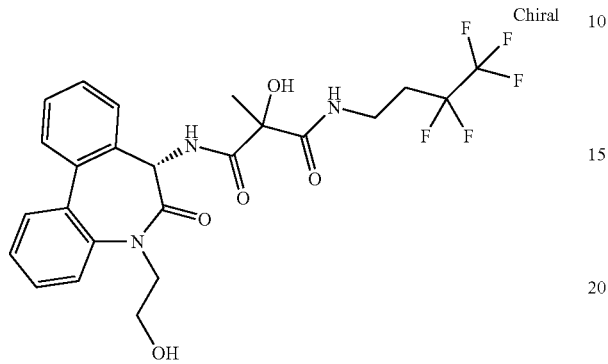

Separation of 2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide (HPLC on Chiralpak AD, eluent 20% ethanol in heptane) afforded the title compound as second eluting material with negative rotation. White solid (72% of th.). MS: m/e=530(M+H$^+$).

EXAMPLE 63

N—[(S)-5-(2-Benzyloxy-ethyl)-6-oxo-6,7-dihydro-5H-dibenzo[b,d]azepin-7-yl]-2-hydroxy-2-methyl-N'-(3,3,3-trifluoro-propyl)-malonamide

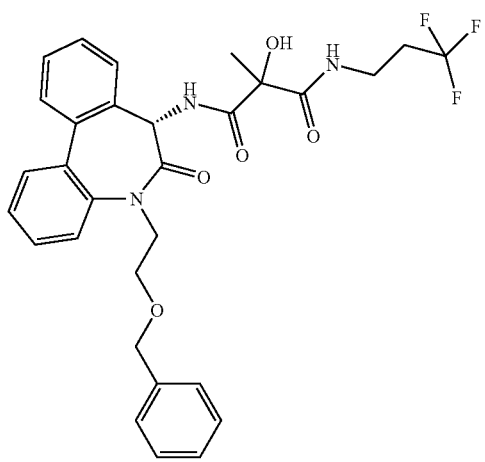

Using (S)-7-amino-5-(2-benzyloxy-ethyl)-5H,7H-dibenzo[b,d]azepin-6-one and 2-hydroxy-2-methyl-N-(3,3,3-trifluoro-propyl)-malonamic acid, the title compound was prepared in the same manner as described for example 1c. Colorless, viscous oil (73%). MS: m/e=570(M+H$^+$).

EXAMPLE 64

2-Hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide

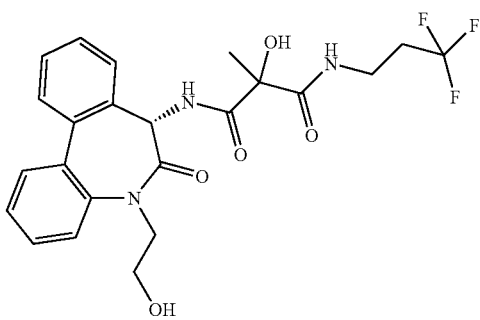

Using N—[(S)-5-(2-benzyloxy-ethyl)-6-oxo-6,7-dihydro-5H-dibenzo[b,d]azepin-7-yl]-2-hydroxy-2-methyl-N'-(3,3,3-trifluoro-propyl)-malonamide, the title compound was prepared in the same manner as example 3 (>98%%). White solid, mp. 59-62° C. MS: m/e=480(M+H$^+$).

EXAMPLE 65

(R or S)-2-Hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, epimer A

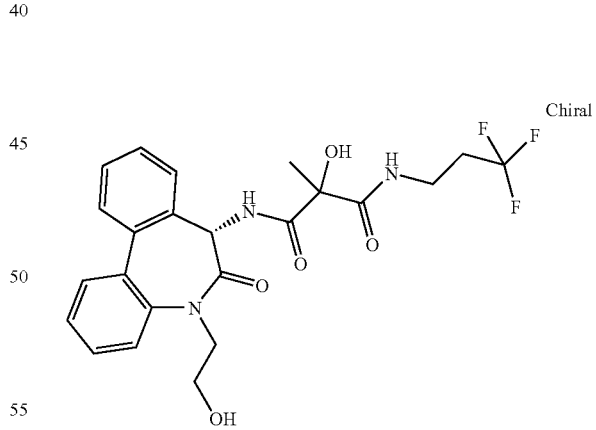

Separation of 2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide (HPLC on Chiralpak AD, eluent 20% ethanol in heptane) afforded the title compound as second eluting material with negative rotation. Off-white solid, mp. 61-69° C. (76% of th.). MS: m/e=480(M+H$^+$).

EXAMPLE 66

(S or R)-2-Hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, epimer B

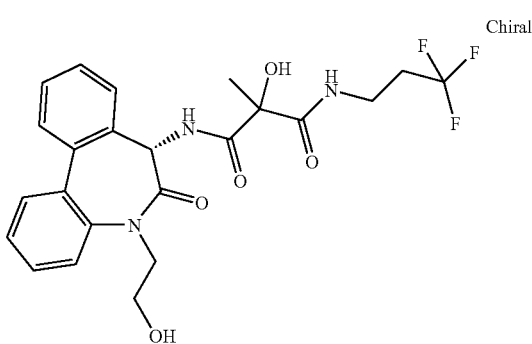

Separation of 2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide (HPLC on Chiralpak AD, eluent 20% ethanol in heptane) afforded the title compound as second eluting material with negative rotation. Off-white solid, mp 64-71° C. (79% of th.). MS: m/e=480(M+H$^+$).

EXAMPLE 67

N—[(S)-5-(2-Methoxy-ethyl)-6-oxo-6,7-dihydro-5H-dibenzo[b,d]azepin-7-yl]-2,2-dimethyl-N'-(2,2,3,3,3-pentafluoro-propyl)-malonamide

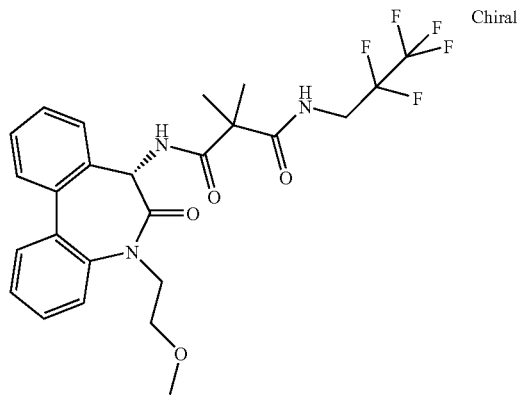

Using (S)-7-amino-5-(2-methoxy-ethyl)-5H,7H-dibenzo[b,d]azepin-6-one and 2,2-dimethyl-N-(2,2,3,3,3-pentafluoro-propyl)-malonamic acid, the title compound was prepared in the same manner as example 1c (74%). White solid. MS: m/e=528(M+H$^+$).

EXAMPLE 68

2-Methoxy-N—[(S)-5-(2-methoxy-ethyl)-6-oxo-6,7-dihydro-5H-dibenzo[b,d]azepin-7-yl]-N'-(2,2,3,3,3-pentafluoro-propyl)-malonamide

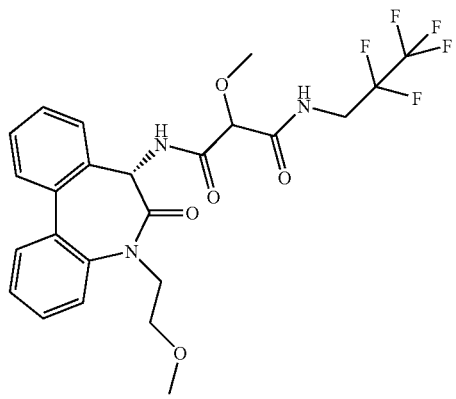

Using (S)-7-amino-5-(2-methoxy-ethyl)-5H,7H-dibenzo[b,d]azepin-6-one and 2-methoxy-N-(2,2,3,3,3-pentafluoro-propyl)-malonamic acid, the title compound was prepared in the same manner as example 1c (84%). White solid. MS: m/e=530(M+H$^+$).

EXAMPLE 69

N-{(S)-5-[2-(4-Fluoro-phenoxy)-ethyl]-6-oxo-6,7-dihydro-5H-dibenzo[b,d]azepin-7-yl}-2,2-dimethyl-N'-(2,2,3,3,3-pentafluoro-propyl)-malonamide a) [(S)-5-[2-(4-fluoro-phenoxy)-ethyl]-6-oxo-6,7-dihydro-5H-dibenzo[b,d]azepin-7-yl]-carbamic acid tert-butyl ester

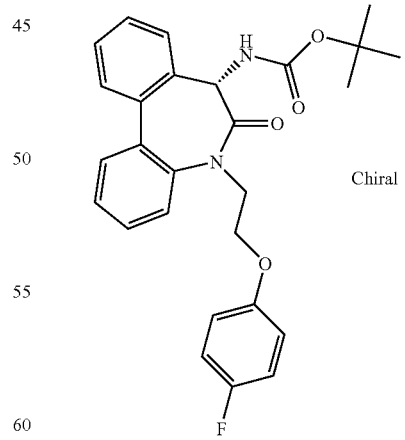

Using ((S)-6-oxo-6,7-dihydro-5H-dibenzo[b,d]azepin-7-yl)-carbamic acid tert-butyl ester and 4-fluorophenoxy-ethylbromide, the title product was prepared in the same manner as described for example 1a (84%). White solid. MS: m/e=463(M+H$^+$).

b) (S)-7-Amino-5-[2-(4-fluoro-phenoxy)-ethyl]-5H, 7H-dibenzo[b,d]azepin-6-one

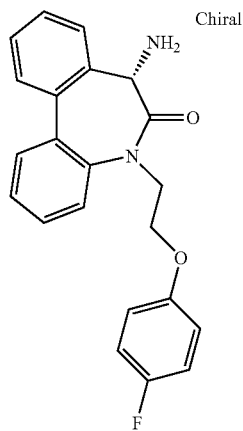

Using [(S)-5-[2-(4-fluoro-phenoxy)-ethyl]-6-oxo-6,7-dihydro-5H-dibenzo[b,d]azepin-7-yl]-carbamic acid tert-butyl ester, the title product was prepared in the same manner as described for example 24b (>98%). Light yellow solid. MS: m/e=363(M+H$^+$).

c) N-{(S)-5-[2-(4-Fluoro-phenoxy)-ethyl]-6-oxo-6,7-dihydro-5H-dibenzo[b,d]azepin-7-yl}-2,2-dimethyl-N-(2,2,3,3,3-pentafluoro-propyl)-malonamide

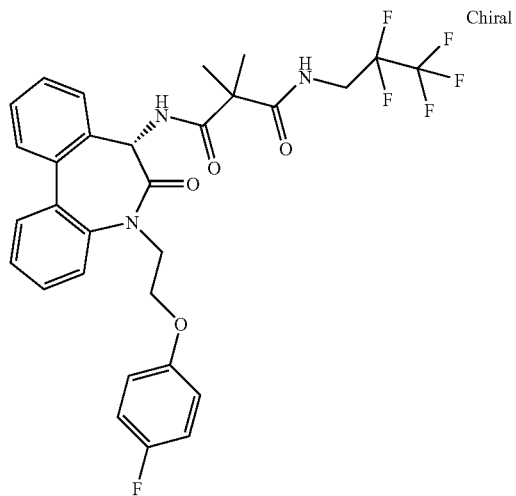

Using (S)-7-Amino-5-[2-(4-fluoro-phenoxy)-ethyl]-5H, 7H-dibenzo[b,d]azepin-6-one and 2,2-dimethyl-N-(2,2,3,3,3-pentafluoro-propyl)-malonamic acid, the title compound was prepared in the same manner as example 1c (85%). White solid. MS: m/e=608(M+H$^+$).

EXAMPLE 70

N—[(S)-5-(2-Isopropoxy-ethyl)-6-oxo-6,7-dihydro-5H-dibenzo[b,d]azepin-7-yl]-2,2-dimethyl-N'-(2,2,3,3,3-pentafluoro-propyl)-malonamide a) [(S)-5-(2-Isopropoxy-ethyl)-6-oxo-6,7-dihydro-5H-dibenzo[b,d]azepin-7-yl]-carbamic acid tert-butyl ester

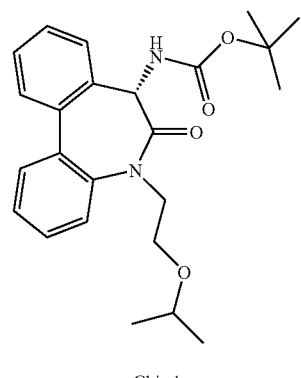

Using ((S)-6-oxo-6,7-dihydro-5H-dibenzo[b,d]azepin-7-yl)-carbamic acid tert-butyl ester and 2-(2-bromo-ethoxy)-propane, the title product was prepared in the same manner as described for example 1a (69%). Pink, viscous oil. MS: m/e=411(M+H$^+$).

b) (S)-7-Amino-5-(2-isopropoxy-ethyl)-5H,7H-dibenzo[b,d]azepin-6-one

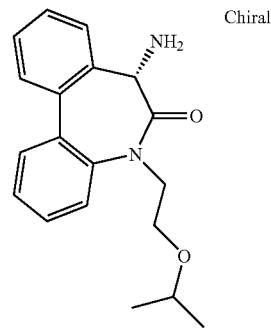

Using [(S)-5-(2-Isopropoxy-ethyl)-6-oxo-6,7-dihydro-5H-dibenzo[b,d]azepin-7-yl]-carbamic acid tert-butyl ester, the title product was prepared in the same manner as described for example 24b (>98%). Light yellow oil. MS: m/e=311 (M+H$^+$).

c) N—[(S)-5-(2-Isopropoxy-ethyl)-6-oxo-6,7-dihydro-5H-dibenzo[b,d]azepin-7-yl]-2,2-dimethyl-N'-(2,2,3,3,3-pentafluoro-propyl)-malonamide

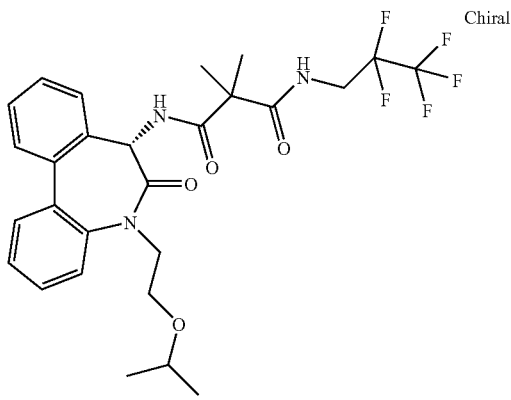

Using (S)-7-Amino-5-(2-isopropoxy-ethyl)-5H,7H-dibenzo[b,d]azepin-6-one and 2,2-dimethyl-N-(2,2,3,3,3-pentafluoro-propyl)-malonamic acid, the title compound was prepared in the same manner as example 1c (78%). White solid. MS: m/e=556(M+H$^+$).

EXAMPLE 71

N—[(S)-5-(2-Ethoxy-ethyl)-6-oxo-6,7-dihydro-5H-dibenzo[b,d]azepin-7-yl]-2,2-dimethyl-N'-(2,2,3,3,3-pentafluoro-propyl)-malonamide a) [(S)-5-(2-Ethoxy-ethyl)-6-oxo-6,7-dihydro-5H-dibenzo[b,d]azepin-7-yl]-carbamic acid tert-butyl ester

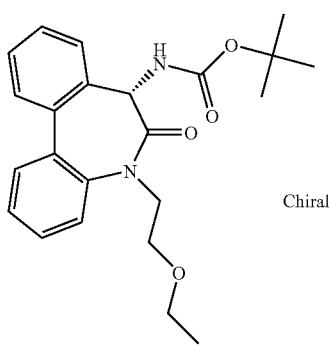

Using ((S)-6-oxo-6,7-dihydro-5H-dibenzo[b,d]azepin-7-yl)-carbamic acid tert-butyl ester and 2-bromomethyl-ethyl ether, the title product was prepared in the same manner as described for example 1a (83%). Pink, viscous oil. MS: m/e=397(M+H$^+$).

b) (S)-7-Amino-5-(2-ethoxy-ethyl)-5H,7H-dibenzo[b,d]azepin-6-one

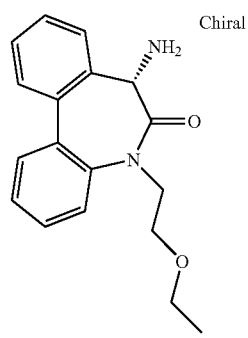

Using [(S)-5-(2-ethoxy-ethyl)-6-oxo-6,7-dihydro-5H-dibenzo[b,d]azepin-7-yl]-carbamic acid tert-butyl ester, the title product was prepared in the same manner as described for example 24b (98%). Yellow oil. MS: m/e=297(M+H$^+$).

c) N—[(S)-5-(2-Ethoxy-ethyl)-6-oxo-6,7-dihydro-5H-dibenzo[b,d]azepin-7-yl]-2,2-dimethyl-N'-(2,2,3,3,3-pentafluoro-propyl)-malonamide

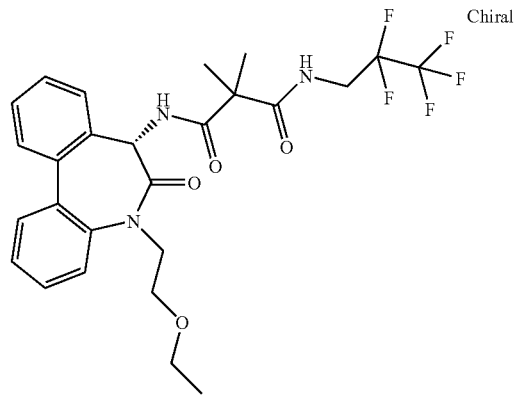

Using (S)-7-amino-5-(2-ethoxy-ethyl)-5H,7H-dibenzo[b,d]azepin-6-one and 2,2-dimethyl-N-(2,2,3,3,3-pentafluoro-propyl)-malonamic acid, the title compound was prepared in the same manner as example 1c (80%). White solid. MS: m/e=542(M+H$^+$).

EXAMPLE 72

2,2-Dimethyl-N—[(S)-6-oxo-5-(3,3,3-trifluoro-2-hydroxy-propyl)-6,7-dihydro-5H-dibenzo[b,d]azepin-7-yl]-N'-(2,2,3,3,3-pentafluoro-propyl)-malonamide a) [(S)-5-(3,3,3-Trifluoro-2-hydroxy-propyl)-6-oxo-6,7-dihydro-5H-dibenzo[b,d]azepin-7-yl]-carbamic acid tert-butyl ester

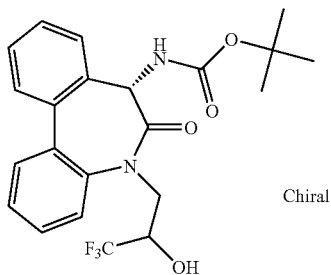

((S)-6-Oxo-6,7-dihydro-5H-dibenzo[b,d]azepin-7-yl)-carbamic acid tert-butyl ester (108 mg, 0.33 mmol) and 1,1,1-trifluoro-2,3-epoxypropane (762 mg, 6.7 mmol) were dissolved in DMF (2 ml) and heated to 90° C. for 4 h in a sealed tube. After addition of another 500 mg of 1,1,1-trifluoro-2,3-epoxypropane, heating was continued for 18 h. The mixture was diluted with ethyl acetate and water (10 ml each), separated and the aqueous phase extracted twice with each 10 ml ethyl acetate. The combine organic phases are dried over magnesium sulfate and evaporated to dryness. Chromatography (silica, eluent heptanes/ethyl acetate gradient from 1 to 30%) afforded the title compound as white solid (76%). MS: m/e=437(M+H$^+$).

b) (S)-7-Amino-5-(3,3,3-trifluoro-2-hydroxy-propyl)-5H,7H-dibenzo[b,d]azepin-6-one

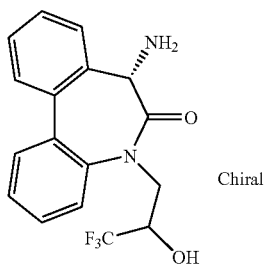

Using [(S)-5-(3,3,3-trifluoro-2-hydroxy-propyl)-6-oxo-6,7-dihydro-5H-dibenzo[b,d]azepin-7-yl]-carbamic acid tert-butyl ester, the title product was prepared in the same manner as described for example 24b (>98%). White solid, mp 192-194° C. MS: m/e=337(M+H$^+$).

c) 2,2-Dimethyl-N—[(S)-6-oxo-5-(3,3,3-trifluoro-2-hydroxy-propyl)-6,7-dihydro-5H-dibenzo[b,d]azepin-7-yl]-N'-(2,2,3,3,3-pentafluoro-propyl)-malonamide

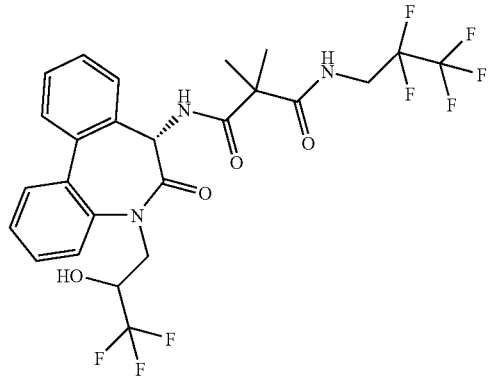

Using (S)-7-amino-5-(3,3,3-trifluoro-2-hydroxy-propyl)-5H,7H-dibenzo[b,d]azepin-6-one and 2,2-dimethyl-N-(2,2,3,3,3-pentafluoro-propyl)-malonamic acid, the title compound was prepared in the same manner as example 1c (87%). White solid. MS: m/e=582(M+H$^+$).

The invention claimed is:
1. A compound of formula I

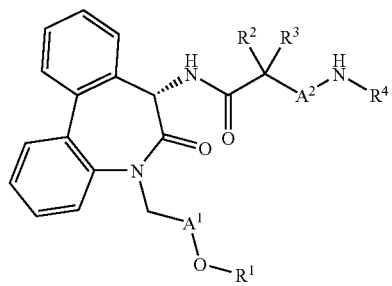

wherein
$A^1$ is —CHR— or —C(O)—;
$A^2$ is —C(O)— and
$R^2$ and $R^3$ are each independently hydrogen, lower alkyl, halogen, hydroxy or lower alkoxy; or
$A^2$ is —O—C(O)— and
$R^2$ and $R^3$ are each independently hydrogen or lower alkyl;
R is hydrogen or lower alkyl substituted by halogen;
$R^1$ is hydrogen, or is lower alkyl or —(CH$_2$)$_n$-aryl, each of which is optionally substituted by halogen;
$R^4$ is lower alkyl substituted by halogen; and
n is 0, 1 or 2;
or a pharmaceutically acceptable acid addition salt, optically pure enantiomer, racemate or diastereomeric mixture thereof.

2. A compound of claim 1, wherein $A^1$ is CH$_2$, $A^2$ is CO, $R^1$ is hydrogen or lower alkyl.

3. A compound of claim 2, selected from the group consisting of
N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide, N—[(S)-5-(2-hydroxy-ethyl)-6-oxo-6,7-dihydro-5H-dibenzo[b,d]azepin-7-yl]-2,2-dimethyl-N'-(2,2,3,3,3-pentafluoro-propyl)-malonamide,
N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide,
N—[(S)-5-(2-hydroxy-ethyl)-6-oxo-6,7-dihydro-5H-dibenzo[b,d]azepin-7-yl]-2-methoxy-N'-(2,2,3,3,3-pentafluoro-propyl)-malonamide,
2-hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide,
2-fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide,
2-ethoxy-N—[(S)-5-(2-hydroxy-ethyl)-6-oxo-6,7-dihydro-5H-dibenzo[b,d]azepin-7-yl]-N '-(2,2,3,3,3-pentafluoro-propyl)-malonamide,
(S or R)-2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, epimer A, and
[R or S]2-ethoxy-N—[(S)-5-(2-hydroxy-ethyl)-6-oxo-6,7-dihydro-5H-dibenzo[b,d]azepin-7-yl]-N'-(2,2,3,3,3-pentafluoro-propyl)-malonamide, epimer B.

4. A compound of claim 2, selected from the group consisting of
2-hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide, epimer A,
2-hydroxy-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide epimer B,
N—[(S)-5-(2-methoxy-ethyl)-6-oxo-6,7-dihydro-5H-dibenzo[b,d]azepin-7-yl]-N'-(2,2,3,3,3-pentafluoro-propyl)-malonamide,
(R)-2-fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide,
(S)-2-fluoro-N—[(S)-5-(2-hydroxy-ethyl)-6-oxo-6,7-dihydro-5H-dibenzo[b,d]azepin-7-yl]-2-methyl-N'-(2,2,3,3,3-pentafluoro-propyl)-malonamide,
N—[(S)-5-(2-hydroxy-ethyl)-6-oxo-6,7-dihydro-5H-dibenzo[b,d]azepin-7-yl]-N'-(3,3,3-trifluoro-propyl)-malonamide,
N—[(S)-5-(2-hydroxy-ethyl)-6-oxo-6,7-dihydro-5H-dibenzo[b,d]azepin-7-yl]-N'-(3,3,4,4,4-pentafluoro-butyl)-malonamide,
(R)-2-fluoro-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, and
(R)-2-fluoro-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide.

5. A compound of claim 2, selected from the group consisting of
(R)-2-fluoro-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide,
2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide,
(R)-2-hydroxy-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide,
(S)-2-hydroxy-N—[(S)-5-(2-hydroxy-ethyl)-6-oxo-6,7-dihydro-5H-dibenzo[b,d]azepin-7-yl]-2-methyl-N'-(2,2,2-trifluoro-ethyl)-malonamide,
(R or S)-2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, epimer A,
(S or R)-2-hydroxy-N—[(S)-5-(2-hydroxy-ethyl)-6-oxo-6,7-dihydro-5H-dibenzo[b,d]azepin-7-yl]-2-methyl-N'-(3,3,4,4,4-pentafluoro-butyl)-malonamide, epimer B,
2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide,
(R or S)-2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, epimer A and
(S or R)-2-hydroxy-N—[(S)-5-(2-hydroxy-ethyl)-6-oxo-6,7-dihydro-5H-dibenzo[b,d]azepin-7-yl]-2-methyl-N'-(3,3,3-trifluoro-propyl)-malonamide, epimer B.

6. A compound of claim 1, wherein $A^1$ is $CH_2$, $A^2$ is O—CO and $R^1$ is hydrogen or lower alkyl.

7. A compound of claim 6, selected from the group consisting of
(2,2,3,3,3-pentafluoro-propyl)-carbamic acid (S)-1-[(S)-5-(2-hydroxy-ethyl)-6-oxo-6,7-dihydro-5H-dibenzo[b,d]azepin-7-ylcarbamoyl]-ethyl ester,
(2,2,3,3,3-pentafluoro-propyl)-carbamic acid (S)-1-[(S)-5-(2-methoxy-ethyl)-6-oxo-6,7-dihydro-5H-dibenzo[b,d]azepin-7-ylcarbamoyl]-ethyl ester,
(3,3,4,4,4-pentafluoro-butyl)-carbamic acid (S)-1-[(S)-5-(2-hydroxy-ethyl)-6-oxo-6,7-dihydro-5H-dibenzo[b,d]azepin-7-ylcarbamoyl]-ethyl ester,
(3,3,3-trifluoro-propyl)-carbamic acid (S)-1-[(S)-5-(2-hydroxy-ethyl)-6-oxo-6,7-dihydro-5H-dibenzo[b,d]azepin-7-ylcarbamoyl]-ethyl ester,
(2-fluoro-ethyl)-carbamic acid (S)-1-[(S)-5-(2-hydroxy-ethyl)-6-oxo-6,7-dihydro-5H-dibenzo[b,d]azepin-7-yl-carbamoyl]-ethyl ester and
(2,2,2-trifluoro-ethyl)-carbamic acid (S)-1-[(S)-5-(2-hydroxy-ethyl)-6-oxo-6,7-dihydro-5H-dibenzo[b,d]azepin-7-ylcarbamoyl]-ethyl ester.

8. A compound of claim 1, wherein $A^1$ is $CHCF_3$, $A^2$ is CO and $R^1$ is hydrogen or lower alkyl.

9. A compound of claim 8, which is
2,2-dimethyl-N—[(S)-6-oxo-5-(3,3,3-trifluoro-2-hydroxy-propyl)-6,7-dihydro-5H-dibenzo[b,d]azepin-7-yl]-N'-(2,2,3,3,3-pentafluoro-propyl)-malonamide.

10. A pharmaceutical composition comprising a compound of formula I

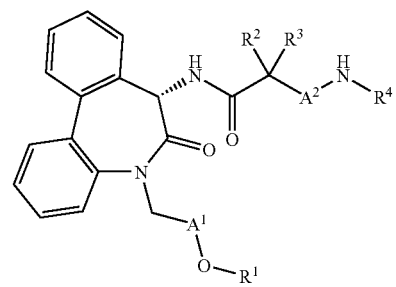

wherein
$A^1$ is —CHR— or —C(O)—;
$A^2$ is —C(O)— and
$R^2$ and $R^3$ are each independently hydrogen, lower alkyl, halogen, hydroxy or lower alkoxy; or $A^2$ is —O—C(O)— and $R^2$ and $R^3$ are each independently hydrogen or lower alkyl;

R is hydrogen or lower alkyl substituted by halogen;

$R^1$ is hydrogen, or is lower alkyl or —$(CH_2)_n$-aryl, each of which is optionally substituted by halogen;

$R^4$ is lower alkyl substituted by halogen; and n is 0, 1 or 2;

or a pharmaceutically acceptable acid addition salt, optically pure enantiomer, racemate or diastereomeric mixture thereof and a pharmaceutically acceptable carrier.

* * * * *